United States Patent
Ju et al.

(10) Patent No.: US 10,231,332 B2
(45) Date of Patent: Mar. 12, 2019

(54) INORGANIC FILLER AND EPOXY RESIN COMPOSITION INCLUDING THE SAME

(71) Applicant: LG INNOTEK CO., LTD., Seoul (KR)

(72) Inventors: Sanga Ju, Seoul (KR); Jina Gu, Seoul (KR); Se Woong Na, Seoul (KR); Sung Jin Yun, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 343 days.

(21) Appl. No.: 14/827,423

(22) Filed: Aug. 17, 2015

(65) Prior Publication Data
US 2016/0081188 A1    Mar. 17, 2016

(30) Foreign Application Priority Data
Sep. 12, 2014  (KR) .................. 10-2014-0121060

(51) Int. Cl.
| | | |
|---|---|---|
| C09D 1/00 | (2006.01) | |
| C08K 9/08 | (2006.01) | |
| H05K 1/03 | (2006.01) | |
| C08K 9/04 | (2006.01) | |
| H05K 1/05 | (2006.01) | |
| C07F 5/05 | (2006.01) | |
| C09C 1/00 | (2006.01) | |
| C09C 3/08 | (2006.01) | |
| C08K 3/38 | (2006.01) | |
| H05K 3/46 | (2006.01) | |

(52) U.S. Cl.
CPC ............ *H05K 1/0373* (2013.01); *C07F 5/05* (2013.01); *C08K 9/04* (2013.01); *C08K 9/08* (2013.01); *C09C 1/00* (2013.01); *H05K 1/056* (2013.01); *C08K 2003/382* (2013.01); *C09C 3/08* (2013.01); *H05K 3/4676* (2013.01); *H05K 2201/0209* (2013.01)

(58) Field of Classification Search
CPC .... C09C 1/00; C09C 3/08; C08K 9/08; C08L 63/00
See application file for complete search history.

(56) References Cited

U.S. PATENT DOCUMENTS

| | | | | |
|---|---|---|---|---|
| 6,160,042 A | * | 12/2000 | Ishida ................ | C08K 9/04 423/290 |
| 8,258,346 B2 | * | 9/2012 | Rajendran ............ | C07C 211/46 428/195.1 |
| 8,784,980 B2 | * | 7/2014 | Lin ..................... | C08K 9/04 428/220 |
| 2013/0143981 A1 | * | 6/2013 | Miyata ............... | C08G 59/245 523/223 |

FOREIGN PATENT DOCUMENTS

| | | |
|---|---|---|
| CN | 103068875 A | 4/2013 |
| JP | 62167318 A  * | 7/1987 |
| WO | 2012/026012 A1 | 3/2012 |

OTHER PUBLICATIONS

SIPO Office Action for Chinese Application No. 2015105146555 dated Feb. 24, 2018, which corresponds to the above-referenced U.S. application.

* cited by examiner

*Primary Examiner* — Vickey Nerangis
(74) *Attorney, Agent, or Firm* — LRK Patent Law Firm

(57) ABSTRACT

An inorganic filler includes surface-modified boron nitride having a surface on which a polycyclic aromatic hydrocarbon having a functional group is provided.

14 Claims, 10 Drawing Sheets

INORGANIC FILLER AND EPOXY RESIN COMPOSITION INCLUDING THE SAME

CROSS-REFERENCE TO RELATED APPLICATION

This application claims priority to and the benefit of Korean Patent Application No. 2014-0121060, filed on Sep. 12, 2014, the disclosure of which is incorporated herein by reference in its entirety.

BACKGROUND

1. Field of the Invention

The present invention relates to an inorganic filler, and more particularly, to an inorganic filler included in an epoxy resin composition.

2. Discussion of Related Art

A light emitting device including a light emitting element such as a light emitting diode (LED) is applied to various light sources. With the development of semiconductor technology, a trend toward a high output light emitting element is accelerating. To stably cope with great amounts of light and heat emitted from such a light emitting element, a heat dissipating performance of the light emitting element is required.

Also, because of highly-integrated and high-capacity electronic parts, an interest in heat dissipation for a printed circuit board on which such electronic parts are mounted is growing.

Generally, for an insulating layer of a light emitting element or printed circuit board, an epoxy resin composition including an epoxy compound, a curing agent and an inorganic filler may be used.

Here, the inorganic filler may include boron nitride. However, the boron nitride has excellent thermal conductivity, heat dissipation performance and electrical insulation, but has a low affinity to the epoxy compound due to a smooth surface, thereby having a low dispersibility, a low adhesive strength to a substrate, and a low workability.

SUMMARY OF THE INVENTION

The present invention is directed to providing an inorganic filler, an, epoxy resin composition including the same, and a printed circuit board.

One aspect of the present invention provides an organic filler, which includes surface-modified boron nitride having a surface on which a polycyclic aromatic hydrocarbon having a functional group is provided.

The polycyclic aromatic hydrocarbon may include at least one selected from the group consisting of naphthalene, anthracene and pyrene.

The functional group may be selected from the group consisting of —OH, —NH$_2$, —COOH, —HSO$_3$, —NH$_2$CO, Cl, Br, F, C$_1$ to C$_3$ alkyls, C$_2$ to C$_3$ alkenes, and C$_2$ to C$_3$ alkynes.

The inorganic filler may include the boron nitride at 85 to 99 vol % and the polycyclic aromatic hydrocarbon at 1 to 15 vol %.

Another aspect of the present invention provides an epoxy resin composition, which includes an epoxy compound, and an inorganic filler, which includes surface-modified boron nitride having a surface on which a polycyclic aromatic hydrocarbon having a functional group is provided.

The volumetric ratio of the epoxy compound and the inorganic filler may be 10:30 to 120.

Still another aspect of the present invention provides a printed circuit board, which includes a substrate, an insulating layer formed on the substrate, and a circuit pattern formed on the insulating layer, wherein the insulating layer includes an epoxy resin composition. The epoxy resin composition includes an epoxy compound and, and an inorganic filler, which includes surface-modified boron nitride having a surface on which a polycyclic aromatic hydrocarbon having a functional group is provided.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
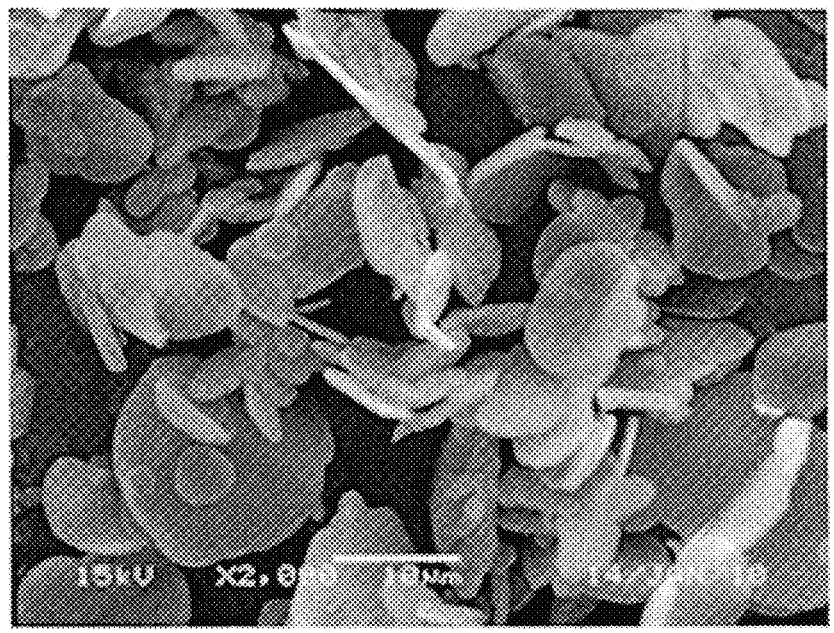
FIG. 1 is the scanning electron microscope (SEM) image of hexagonal boron nitride before surface modification.

The present invention may have various modifications and various exemplary embodiments and specific exemplary embodiments will be illustrated in the drawings and described. However, it is not intended to limit the present invention to the specific exemplary embodiments, and it should be understood that the present invention covers all the modifications, equivalents and replacements included in the spirit and technical scope of the present invention.

Terms including an ordinal number such as "first" or "second" may be used to describe various components but the components are not limited by the above terms. The above terms are used only to discriminate one component from another component. For example, without departing from the scope of the present invention, a second component may be referred to as a first component, and similarly, the first component may be referred to as the second component. The term "and/or" includes a combination of a plurality of associated disclosed items or any item of the plurality of associated disclosed items.

Terms used in the present application are used only to describe specific exemplary embodiments, and are not intended to limit the present invention. Singular expressions used herein include plurals expressions unless they have definitely opposite meanings in the context. In the present application, it should be understood that the term "include" or "have" indicates that a feature, a number, a step, an operation, a component, a part or the combination thereof described in the specification is present, but does not exclude a possibility of presence or addition of one or more other features, numbers, steps, operations, components, parts or combinations thereof, in advance.

Unless otherwise defined, all terms used herein including, technological or scientific terms have the same meanings as those generally understood by a person with ordinary skill in the art to which the present invention pertains. It should be understood that terms defined in a generally used dictionary have the same meanings as contextual meanings of associated techniques and if not apparently defined in this application, the terms shall not be construed to have idealistic or excessively formal meanings.

When a component of a layer, film, region or plate is placed "on" a different component, the component may be placed "directly on" the other component, or a third component may intervene between the two components. In contrast, when a component is placed "directly on" a different component, there are no intervening components between the two components.

Hereinafter, with reference to the accompanying drawings, exemplary embodiments will be described in detail, and regardless of the reference marks on the drawings, like reference numerals will be assigned to the like or corresponding components, and duplicated descriptions thereof will be omitted.

An epoxy resin composition according to a first exemplary embodiment includes an epoxy compound and an inorganic filler. Here, the inorganic filler includes surface-modified hexagonal boron nitride having a surface on which a polycyclic aromatic hydrocarbon having a functional group is provided.

To be specific, the epoxy resin composition according to the first exemplary embodiment may include the epoxy compound and the inorganic filler at a volumetric ratio of 10:30 to 120, preferably, 10:36 to 90, and more preferably, 10:44 to 60. When the inorganic filler is included at less than the above-described numerical range, thermal conductivity may be degraded. On the other hand, when the inorganic filler is included at greater than the above-described numerical range, the brittleness of the epoxy resin composition may be increased, leading to a decrease in peel strength.

Here, the epoxy compound may include at least one of a crystalline epoxy compound, an amorphous epoxy compound, and a silicon epoxy compound.

The crystalline epoxy compound may have a mesogen structure. The mesogen is the basic unit of a liquid crystal, and has a rigid structure.

Also, the amorphous epoxy compound may be a conventional amorphous epoxy compound having two or more epoxy groups, for example, a glycidyl ether compound derived from bisphenol A or bisphenol F. The amorphous epoxy compound may be included at 3 to 40 parts by volume with respect to 10 parts by volume of the crystalline epoxy compound. When the crystalline epoxy compound and the amorphous epoxy compound are included at the above-described ratio, room temperature stability may be improved.

Also, the silicon epoxy compound may be included at 3 to 40 parts by volume with respect to 10 parts by volume of the crystalline epoxy compound. When the epoxy compound and the silicon epoxy compound are included at the above-described ratio, thermal conductivity and thermal resistance may be improved.

Also, the epoxy resin composition according to the first exemplary embodiment may further include a curing agent. The curing agent may be included at 1 to 5 parts by volume with respect to 10 parts by volume of the epoxy compound. The curing agent included in the epoxy resin composition according to the first exemplary embodiment may include at least one of an amine-based curing agent, a phenol-based curing agent, an acid anhydride-based curing agent, a polymercaptan-based curing agent, a polyaminoamide-based curing agent, an isocyanate-based curing agent and a block isocyanate-based curing agent, or may be used in combination of at least two thereof. The amine-based curing agent may include, for example, diaminodiphenyl sulfone (DAS).

Also, the epoxy resin composition according to the first exemplary embodiment includes the inorganic filler, which includes surface-modified hexagonal boron nitride having a surface on which a polycyclic aromatic hydrocarbon having a functional group is provided. Hereinafter, the inorganic filler included in the epoxy resin composition according to the first exemplary embodiment will be described in further detail.

Figure 2:
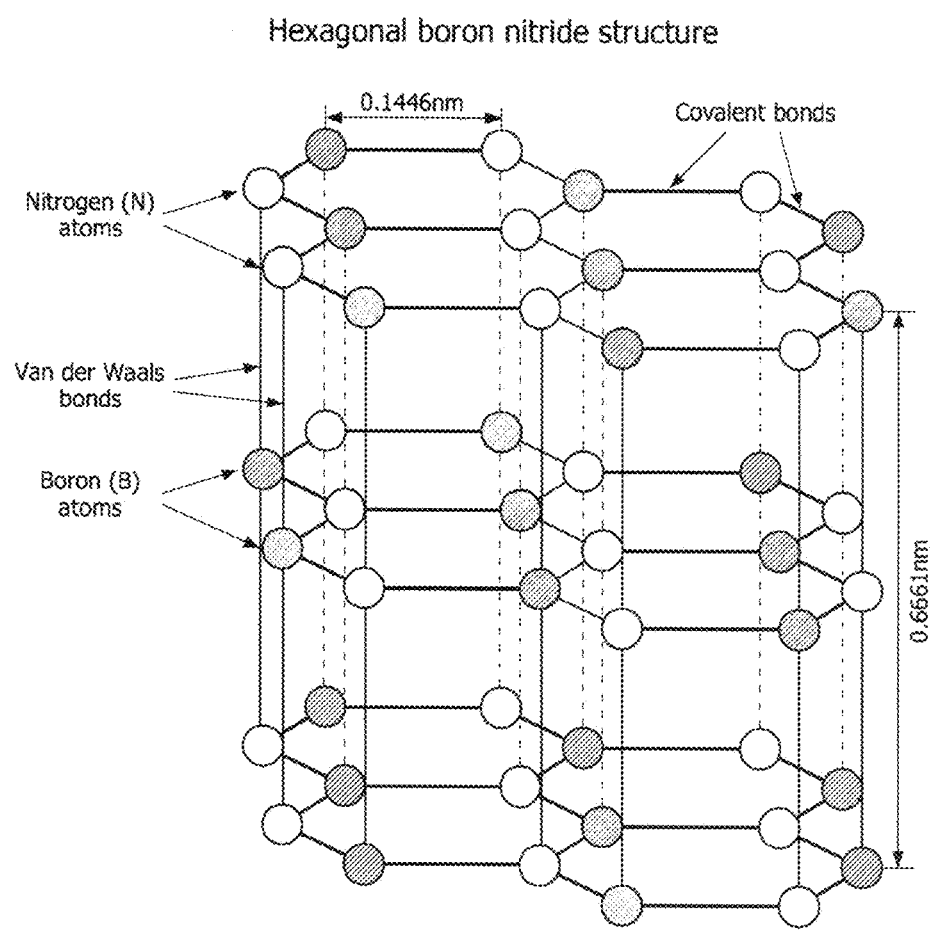
FIG. 2 shows the structure of the hexagonal boron nitride before surface modification.

FIG. 1 is the SEM image of hexagonal boron nitride before surface modification, and FIG. 2 shows the structure of the hexagonal boron nitride before surface modification.

Referring to FIGS. 1 and 2, nitrogen atoms and boron atoms are alternately arranged, thereby forming a hexagonal lattice, and a plurality of hexagonal lattices may be arranged on a plane. In addition, the hexagonal boron nitride may be stacked in layers. In the specification, the plurality of hexagonal lattices arranged on one plane may be expressed as a boron nitride layer. The size of the boron nitride may vary with the number of the hexagonal lattices linked on the same plane and stacked. The size of the boron nitride applied to the exemplary embodiment of the present invention is not particularly limited, but the width and height of the boron nitride may be in the range from 1 to 20 μm.

The hexagonal boron nitride has very excellent thermal conductivity, heat dissipation performance and electrical insulation, but has a low coefficient of friction of 0.15 to 0.70, thereby having a smooth surface, and low wettability, and is chemically inactive.

When a functional group is provided to the surface of the hexagonal boron nitride, the affinity between the boron nitride and the epoxy compound may be increased, and an epoxy resin composition having a high thermal conductivity and a high peel strength may be obtained. However, since the hexagonal boron nitride is chemically inactive, a functional group may not be directly provided to the surface of the hexagonal boron nitride.

According to an exemplary embodiment of the present invention, the surface of the hexagonal boron nitride is to be modified using a polycyclic aromatic hydrocarbon having a functional group. In the specification, the polycyclic aromatic hydrocarbon having a functional group may be used in combination with an additive. The polycyclic aromatic hydrocarbon refers to an organic compound in which two or more aromatic rings are fused, and may be selected from the group consisting of, for example, naphthalene of Formula 1, anthracene of Formula 2, and pyrene of Formula 3.

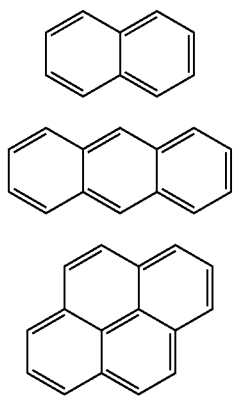

[Formula 1]

[Formula 2]

[Formula 3]

Figure 3:
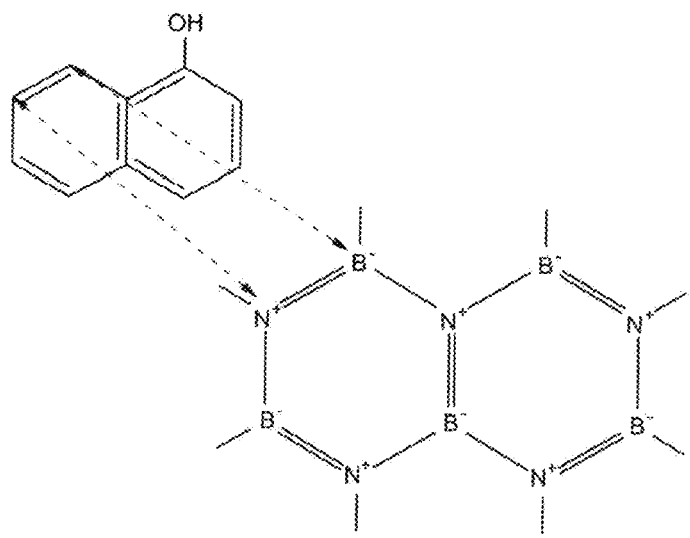
FIG. 3 shows the bonds between a polycyclic aromatic hydrocarbon and the hexagonal boron nitride according to an exemplary embodiment of the present invention.

As shown in Formulas 1 to 3, the polycyclic aromatic hydrocarbon has a structure similar to the hexagonal boron nitride shown in FIG. 2. For this reason, the affinity between the polycyclic aromatic hydrocarbon and the hexagonal boron nitride is high. When the polycyclic aromatic hydrocarbon is used, a similar effect to direct binding of a functional group to the hexagonal boron nitride can be acquired. Here, the functional group included in the polycyclic aromatic hydrocarbon may be selected from the group consisting of —OH, —NH$_2$, —COOH, —HSO$_3$, —NH$_2$CO, Cl, Br, F, C$_1$ to C$_3$ alkyls, C$_2$ to C$_3$ alkenes, and C$_2$ to C$_3$ alkynes. FIG. 3 shows the bonds between a polycyclic aromatic hydrocarbon and the hexagonal boron nitride according to an exemplary embodiment of the present invention. In the case of hexagonal boron nitride in which a plurality of boron nitride layers are stacked, a polycyclic aromatic hydrocarbon having a functional group may be bonded to at least one of the uppermost boron nitride layer and the lowermost boron nitride layer. Alternatively, the polycyclic aromatic hydrocarbon having a functional group may be provided between the plurality of boron nitride layers.

As described above, when the hexagonal boron nitride is surface-modified using the polycyclic aromatic hydrocarbon having a functional group, the wettability between the surface-modified boron nitride and the epoxy compound is increased, and the dispersibility and peel strength may be improved.

Here, the surface-modified boron nitride may include 85 to 99 vol % of the boron nitride and 1 to 15 vol % of the polycyclic aromatic hydrocarbon, and preferably 88 to 97 vol % of the boron nitride and 3 to 12 vol % of the polycyclic aromatic hydrocarbon, with respect to 100 vol % of the inorganic filler. When the boron nitride is included above the above-described numerical range, the amount of the polycyclic aromatic hydrocarbon is relatively reduced, and the amount of the functional group provided is reduced, and thus it is difficult to raise the peel strength. In addition, when the boron nitride is included below the above-described numerical range, the amount of residual polycyclic aromatic hydrocarbons that does not participate in the reaction is relatively increased, which may have an adverse effect on thermal conductivity.

Figure 4:
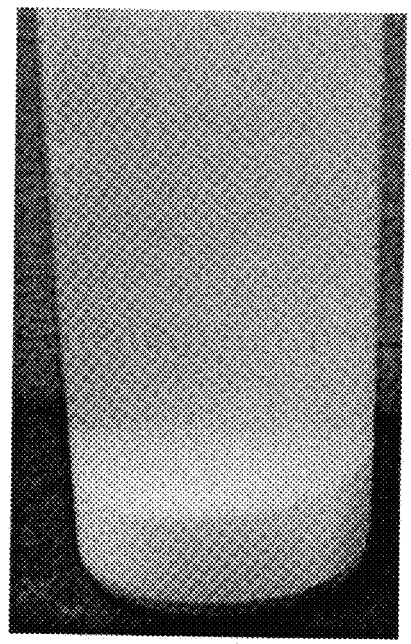
FIGS. 4 and 5 are images showing dispersibility of the surface-modified hexagonal boron nitride according to an exemplary embodiment of the present invention.
Figure 5:
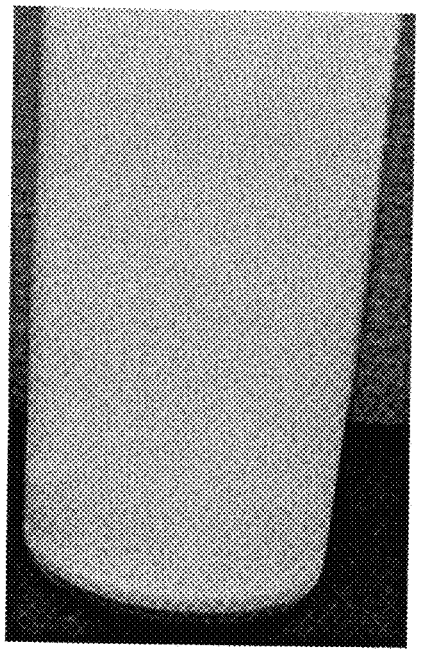

FIGS. 4 to 5 are images showing the dispersibility of surface-modified hexagonal boron nitride according to an exemplary embodiment of the present invention.

FIG. 4 is an image obtained by putting 1 g of hexagonal boron nitride and 15 ml of methyl ethyl ketone (MEK) into a 20-ml glass bottle, mixing the resulting mixture for 10 minutes, and maintaining the mixture for 1 hour, and FIG. 5 is an image obtained by putting 1 g of surface-modified hexagonal boron nitride (prepared by mixing hexagonal boron nitride and naphthalene having a hydroxyl group at a volumetric ratio of 80:20 according to an exemplary embodiment of the present invention) and 15 ml of MEK into a 20-ml glass bottle, mixing the resulting mixture for 10 minutes, and maintaining the mixture for 1 hour.

Comparing FIG. 4 and FIG. 5, it can be seen that the dispersibility of the surface-modified hexagonal boron nitride according to an exemplary embodiment of the present invention is considerably higher than that of non-surface-modified hexagonal boron nitride. As described above, when the surface of the hexagonal boron nitride is modified with a polycyclic aromatic hydrocarbon having a functional group, the dispersibility may be improved. Particularly, when a functional group such as a hydroxyl group (—OH) is provided on the surface of the hexagonal boron nitride, the binding strength between the epoxy resin and the boron nitride may be increased, thereby increasing thermal conductivity and peel strength as well as the dispersibility.

Figure 6:
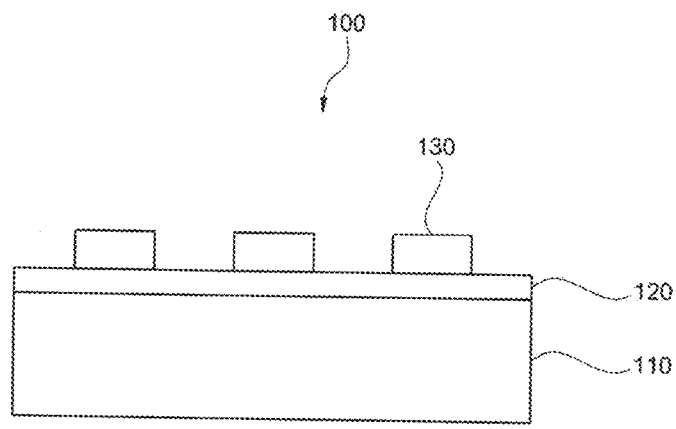
FIG. 6 is a cross-sectional view of a printed circuit board according to an exemplary embodiment of the present invention.

The epoxy resin composition according to an exemplary embodiment of the present invention may be applied to a printed circuit board. FIG. 6 is a cross-sectional view of a printed circuit board according to an exemplary embodiment of the present invention.

Referring to FIG. 6, a printed circuit board 100 includes a substrate 110, an insulating layer 120 and a circuit pattern 130.

The substrate 110 may consist of copper, aluminum, nickel, gold, platinum or an alloy selected therefrom.

The insulating layer 120 consisting of the epoxy resin composition according to an exemplary embodiment of the present invention is formed on the substrate 110.

The circuit pattern 130 is formed on the insulating layer 120. The circuit pattern 130 may consist of a metal such as copper or nickel.

The metal plate 110 and the circuit pattern 130 are insulated by the insulating layer 120.

Figure 7:
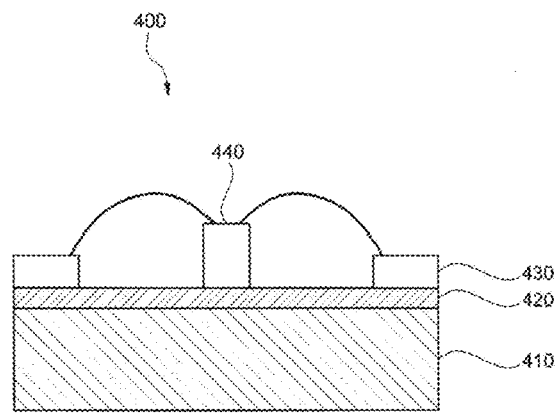
FIG. 7 is a cross-sectional view of a light emitting element module according town exemplary embodiment of the present invention.

The epoxy resin composition including an inorganic filler according to an exemplary embodiment of the present invention may also be applied to a light emitting element module. FIG. 7 is a cross-sectional view of a light emitting element module according to an exemplary embodiment of the present invention.

Referring to FIG. 7, a light emitting element module 400 includes a substrate 410, an insulating layer 420 formed on the substrate 410, a circuit pattern 430 formed on the insulating layer 420, and a light emitting element 440 formed on the insulating layer 420.

The substrate 410 may consist of copper, aluminum, nickel, gold, platinum, or an alloy selected therefrom.

The insulating layer 420 may include the epoxy resin composition including an inorganic filler according to an exemplary embodiment of the present invention.

Although not illustrated, to increase the adhesive strength between the insulating layer 420 and the circuit pattern 430, a seed layer may be formed between the insulating layer 420 and the circuit pattern 430.

Hereinafter, the present invention will be described in further detail with reference to examples and comparative examples.

First, epoxy resin compositions were prepared with the same content ratio of an epoxy compound to boron nitride, and various types of additives.

Example 1-1

15 vol % of the bisphenol A-type epoxy compound of Formula 4, 5 vol % of 4,4'-diaminophenylsulfone and 80 vol % of surface-modified hexagonal boron nitride prepared by mixing naphthalene having a hydroxyl group with hexagonal boron nitride at a volumetric ratio of 5:95 were added to MEK, and stirred for 1 hour. After stirring, a copper plate was uniformly coated with the resulting solution using a coater, and cured under predetermined pressure at 150° C. for 1.5 hours.

[Formula 4]

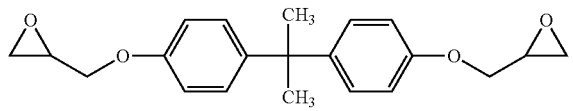

Example 1-2

15 vol % of the bisphenol A-type epoxy compound of Formula 4, 5 vol % of 4,4'-diaminophenylsulfone and 80 vol % of surface-modified hexagonal boron nitride prepared by mixing anthracene having a hydroxyl group with hexagonal boron nitride at a volumetric ratio of 5:95 were added to MEK, and stirred for 1 hour. After stirring, a copper plate was uniformly coated with the resulting solution using a coater, and cured under predetermined pressure at 150° C. for 1.5 hours.

Example 1-3

15 vol % of the bisphenol A-type epoxy compound of Formula 4, 5 vol % of 4,4'-diaminophenylsulfone and 80 vol % of surface-modified hexagonal boron nitride prepared by mixing pyrene having a hydroxyl group with hexagonal boron nitride at a volumetric ratio of 5:95 were added to MEK, and stirred for 1 hour. After stirring, a copper plate was uniformly coated with the resulting solution using a coater, and cured under predetermined pressure at 150° C. for 1.5 hours.

Comparative Example 1-1

15 vol % of the bisphenol A-type epoxy compound of Formula 4, 5 vol % of 4,4'-diaminophenylsulfone and 80 vol % of non-surface-modified hexagonal boron nitride were added to MEK, and stirred for 1 hour. After stirring, a copper plate was uniformly coated with the resulting solution using a coater, and cured under predetermined pressure at 150° C. for 1.5 hours.

Comparative Example 1-2

15 vol % of the bisphenol A-type epoxy compound of Formula 4, 5 vol % of 4,4'-diaminophenylsulfone and 80 vol % of surface-modified hexagonal boron nitride prepared by mixing benzene having a hydroxyl group with hexagonal boron nitride at a volumetric ratio of 5:95 were added to MEK, and stirred for 1 hour. After stirring, a copper plate was uniformly coated with the resulting solution using a coater, and cured under predetermined pressure at 150° C. for 1.5 hours.

Also, additional experiments were carried out with various content ratios of the hexagonal boron nitride to the naphthalene having a hydroxyl group.

Example 1-4

15 vol % of the bisphenol A-type epoxy compound of Formula 4, 5 vol % of 4,4'-diaminophenylsulfone and 80 vol % of surface-modified hexagonal boron nitride prepared by mixing naphthalene having a hydroxyl group with hexagonal boron nitride at a volumetric ratio of 10:90 were added to MEK, and stirred for 1 hour. After stirring, a copper plate was uniformly coated with the resulting solution using a coater, and cured under predetermined pressure at 150° C. for 1.5 hours.

Comparative Example 1-3

15 vol % of the bisphenol A-type epoxy compound of Formula 4, 5 vol % of 4,4'-diaminophenylsulfone and 80 vol % of surface-modified hexagonal boron nitride prepared by mixing naphthalene having a hydroxyl group with hexagonal boron nitride at a volumetric ratio of 1:99 were added to MEK, and stirred for 1 hour. After stirring, a copper plate was uniformly coated with the resulting solution using a coater, and cured under predetermined pressure at 150° C. for 1.5 hours.

Comparative Example 1-4

15 vol % of the bisphenol A-type epoxy compound of Formula 4, 5 vol % of 4,4'-diaminophenylsulfone and 80 vol % of surface-modified hexagonal boron nitride prepared by mixing naphthalene having a hydroxyl group with hexagonal boron nitride at a volumetric ratio of 15:85 were added to MEK, and stirred for 1 hour. After stirring, a copper plate was uniformly coated with the resulting solution using a coater, and cured under predetermined pressure at 150° C. for 1.5 hours.

Also, additional experiments were carried out with various content ratios between an epoxy compound and an inorganic filler, although the content ratio between the hexagonal boron nitride and the naphthalene having a hydroxyl group was equal.

Example 1-5

18 vol % of the bisphenol A-type epoxy compound of Formula 4, 7 vol % of 4,4'-diaminophenylsulfone and 75 vol % of surface-modified hexagonal boron nitride prepared by mixing naphthalene having a hydroxyl group with hexagonal boron nitride at a volumetric ratio of 5:95 were added to MEK, and stirred for 1 hour. After stirring, a copper plate was uniformly coated with the resulting solution using a coater, and cured under predetermined pressure at 150° C. for 1.5 hours.

Example 1-6

11 vol % of the bisphenol A-type epoxy compound of Formula 4, 4 vol % of 4,4'-diaminophenylsulfone and 85 vol % of surface-modified hexagonal boron nitride prepared by mixing naphthalene having a hydroxyl group with hexagonal boron nitride at a volumetric ratio of 5:95 were added to MEK, and stirred for 1 hour. After stirring, a copper plate was uniformly coated with the resulting solution using a coater, and cured under predetermined pressure at 150° C. for 1.5 hours.

Comparative Example 1-5

22 vol % of the bisphenol A-type epoxy compound of Formula 4, 8 vol % of 4,4'-diaminophenylsulfone and 70 vol % of surface-modified hexagonal boron nitride prepared by mixing naphthalene having a hydroxyl group with hexagonal boron nitride at a volumetric ratio of 5:95 were added to MEK, and stirred for 1 hour. After stirring, a copper plate was uniformly coated with the resulting solution using a coater, and cured under predetermined pressure at 150° C. for 1.5 hours.

Comparative Example 1-6

7.5 vol % of the bisphenol A-type epoxy compound of Formula 4, 2.5 vol % of 4,4'-diaminophenylsulfone and 90 vol % of surface-modified hexagonal boron nitride prepared by mixing naphthalene having a hydroxyl group with hexagonal boron nitride at a volumetric ratio of 5:95 were added to MEK, and stirred for 1 hour. After stirring, a copper plate was uniformly coated with the resulting solution using a coater, and cured under predetermined pressure at 150° C. for 1.5 hours.

Experimental Example

The epoxy resin compositions obtained from Examples 1-1 to 1-6 and Comparative Examples 1-1 to 1-6 were cured and then manufactured in a spherical shape having a diameter of 0.5 inches, and a time to equilibrate the lower portion was measured after the upper portion of the sphere was irradiated with laser pulses of 247 voltage, thereby calculating thermal conductivity. Also, after the epoxy resin compositions obtained from Examples 1-1 to 1-6 and Comparative Examples 1-1 to 1-6 were cured, a 62.5-mm-thick copper layer was attached thereon and then lifted in a vertical direction (at an angle of 90°) at a speed of 50 mm/min, thereby measuring peel strength.

Tables 1 to 3 show the measurement results.

TABLE 1

| Experiment No. | Thermal conductivity (w/mK) | Peel strength (kgf/cm$^2$) |
|---|---|---|
| Example 1-1 | 19.32 | 1.03 |
| Example 1-2 | 21.03 | 1.19 |
| Example 1-3 | 22.86 | 1.25 |
| Comparative Example 1-1 | 28.84 | 0.01 |
| Comparative Example 1-2 | 15.65 | 0.72 |

TABLE 2

| Experiment No. | Thermal conductivity (w/mK) | Peel strength (kgf/cm$^2$) |
|---|---|---|
| Example 1-2 | 19.32 | 1.03 |
| Example 1-4 | 18.23 | 1.12 |
| Comparative Example 1-1 | 28.84 | 0 01 |
| Comparative Example 1-3 | 23.51 | 0.64 |
| Comparative Example 1-4 | 13.76 | 1.10 |

TABLE 3

| Experiment No. | Thermal conductivity (w/mK) | Peel strength (kgf/cm$^2$) |
|---|---|---|
| Example 1-2 | 19.32 | 1.03 |
| Example 1 5 | 15.89 | 1.18 |
| Example 1-6 | 22.75 | 0.87 |
| Comparative Example 1-5 | 13.47 | 1.33 |
| Comparative Example 1-6 | 25.61 | 0.72 |

Referring to Table 1, it can be seen that the epoxy resin compositions including the boron nitride surface-modified with the polycyclic aromatic hydrocarbon having a functional group according to Examples 1-1 to 1-3 have excellent thermal conductivity and peel strength. In contrast, it can be seen that the epoxy resin composition including the non-surface-modified boron nitride according to Comparative Example 1-1 has a very low peel strength. Also, it can be seen that since Comparative Example 1-2 including the boron nitride surface-modified with benzene having one aromatic ring has fewer aromatic rings than Examples 1-1 to 1-3, the binding strength between the aromatic ring and the boron nitride is low, and thus the thermal conductivity and peel strength are lower than in Examples 1-1 to 1-3. Meanwhile, it can be seen that the number of aromatic rings are increased from Example 1-1 to 1-3, and thus the binding strength between the aromatic ring, and the boron nitride as well as the thermal conductivity and peel strength are increased.

Referring to Table 2, it can be seen that, when the content ratio between boron nitride and an additive is controlled as described in Examples 1-2 and 1-4, an epoxy resin composition having more excellent thermal conductivity and peel strength can be obtained.

Referring to Table 3, it can be seen that an epoxy resin composition having more excellent thermal conductivity and peel strength can be obtained by controlling the content ratio between the inorganic filler and the epoxy compound as described in Examples 1-2 and 1-5. Particularly, it can be seen that, as described in Example 1-2, when 44 to 60 parts by volume of the inorganic filler was included with respect to 10 parts by volume of the epoxy compound, an epoxy resin composition satisfying all requirements including a thermal conductivity of 16 w/mK or more and a peel strength of 1 kgf/cm can be obtained.

Meanwhile, the epoxy resin composition according to an exemplary embodiment of the present invention may also be applied to a multi-layer printed circuit board. The multi-layer printed circuit board refers to a printed circuit board on which layers of circuit patterns are wired. As the complexity of a circuit is increased, and a demand for a highly-integrated and miniaturized circuit is, increased, a demand for a multi-layer printed circuit board is also increased.

Figure 8:
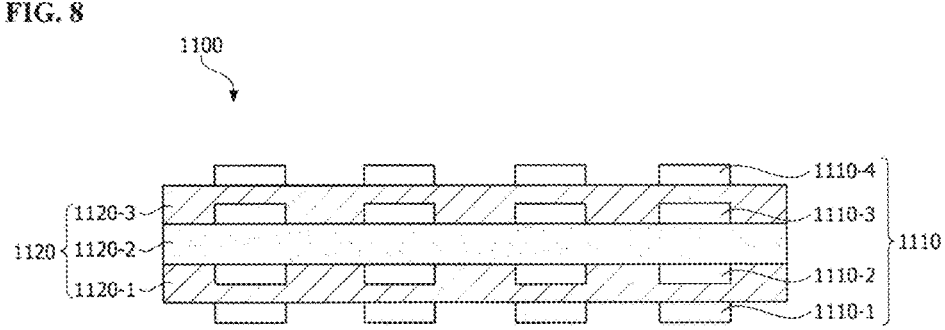
FIG. 8 is a cross-sectional view of a four-layer printed circuit board according to an exemplary embodiment of the present invention.
Figure 9:
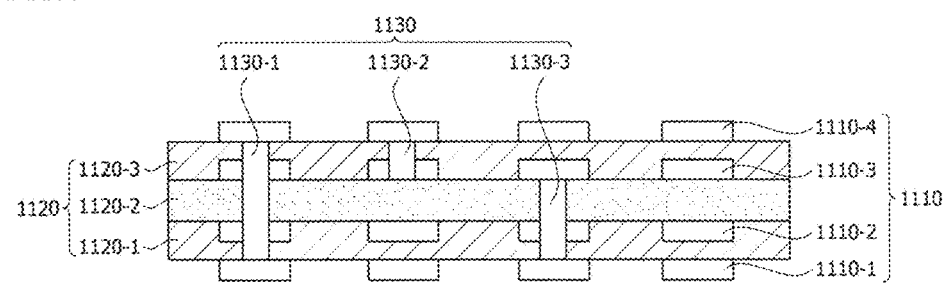
FIG. 9 is a cross-sectional view of a four-layer printed circuit board according to another exemplary embodiment of the present invention.

FIG. 8 is across-sectional view of a four-layer printed circuit board according to an exemplary embodiment of the present invention, and FIG. 9 is a cross-sectional view of a four-layer printed circuit board according to another exemplary embodiment of the present invention.

Referring to FIG. 8, a four-layer printed circuit board 1100 includes a plurality of circuit pattern layers 1110 sequentially disposed, and a plurality of insulating layers 1120 formed between the plurality of circuit pattern layers 1110. That is, the printed circuit board 1100 includes an insulating layer 1120-1 on the bottom of which a circuit pattern layer 1110-1 is formed, an insulating layer 1120-2 on the top and bottom of which circuit pattern layers 1110-2 and 1110-3 are formed, respectively, and an insulating layer 1120-3 on the top of which a circuit pattern layer 1110-4 is formed.

Here, the insulating layer 1120 insulates the circuit pattern layer 1110. Also, the circuit pattern layer 1110 may consist of a metal such as copper or nickel. Although not illustrated in FIG. 8, the four-layer printed circuit board 1100 may be formed on a metal plate. Here, the metal plate may include copper, aluminum, nickel, gold, platinum, or an alloy selected therefrom.

Referring to FIG. 9, the four-layer the printed circuit board 1100 may further include through holes 1130 connecting some of the plurality of circuit pattern layers 1110. That is, a through hole 1130-1 may be formed to pass through the entire printed circuit board 1100, or a through hole 1130-2 or through hole 1130-3 may be formed to pass through a part of the printed circuit board 1100.

The inside of the through holes 1130 may be plated, with copper (Cu), and then filled with an epoxy resin or copper.

Referring to FIGS. 8 and 9, at least one of the insulating layer 1120-1 formed between the circuit pattern layer 1110-1 and the circuit pattern layer 1110-2, which is the lowermost insulating layer 1120-1, and the insulating layer 1120-3 formed between the circuit pattern layer 1110-3 and the circuit pattern layer 1110-4, which is the uppermost insulating layer 1120-3, includes the epoxy resin composition according to an exemplary embodiment of the present invention. Like this, when the insulating layer including the epoxy resin composition having a high thermal conductivity is disposed at at least one of the uppermost and lowermost parts of the printed circuit board, heat generated by a heat emitting element may be dissipated in a vertical direction as well as a horizontal direction.

Here, the thicknesses of the insulating layers 1120-1 and 1120-3 including the epoxy resin composition may range from 30 μm to 1 mm. When the thicknesses of the insulating layers 1120-1 and 1120-3 satisfy the above-described numerical range, a decrease in surface temperature of the printed circuit board may be achieved.

Also, the insulating layer 1120-2 of the plurality of insulating layers may include an epoxy resin-containing glass fiber. The content of the epoxy resin may be 40 to 80 wt % of the insulating layer 1120-2. Here, the epoxy resin may include an amorphous epoxy compound. The amorphous epoxy compound may be a conventional amorphous epoxy compound having two or more epoxy groups in a molecule, for example, a bisphenol A-type epoxy compound, a bisphenol F-type epoxy compound, a cyclic epoxy compound, a novolac-type epoxy compound, or an aliphatic epoxy compound.

The epoxy resin-containing glass fiber may include, for example, FR-4.

Figure 10:
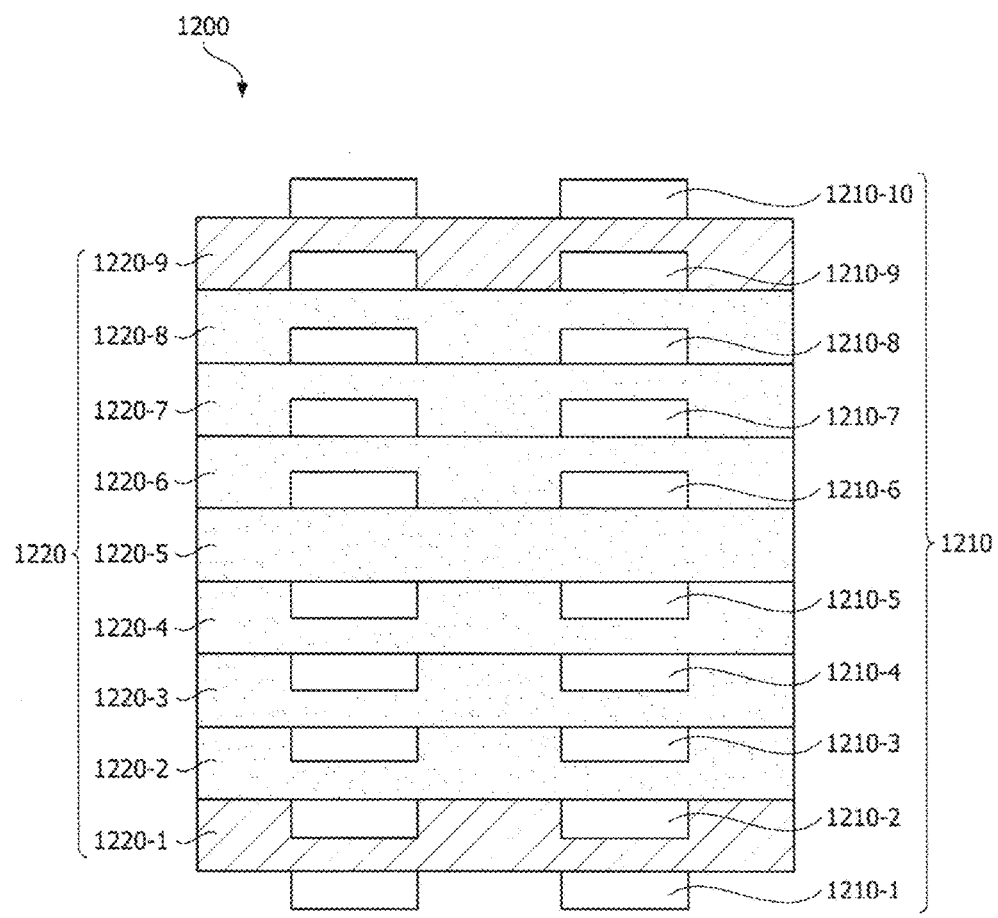
FIG. 10 is a cross-sectional view of a ten-layer printed circuit board according to an exemplary embodiment of the present invention.
Figure 11:
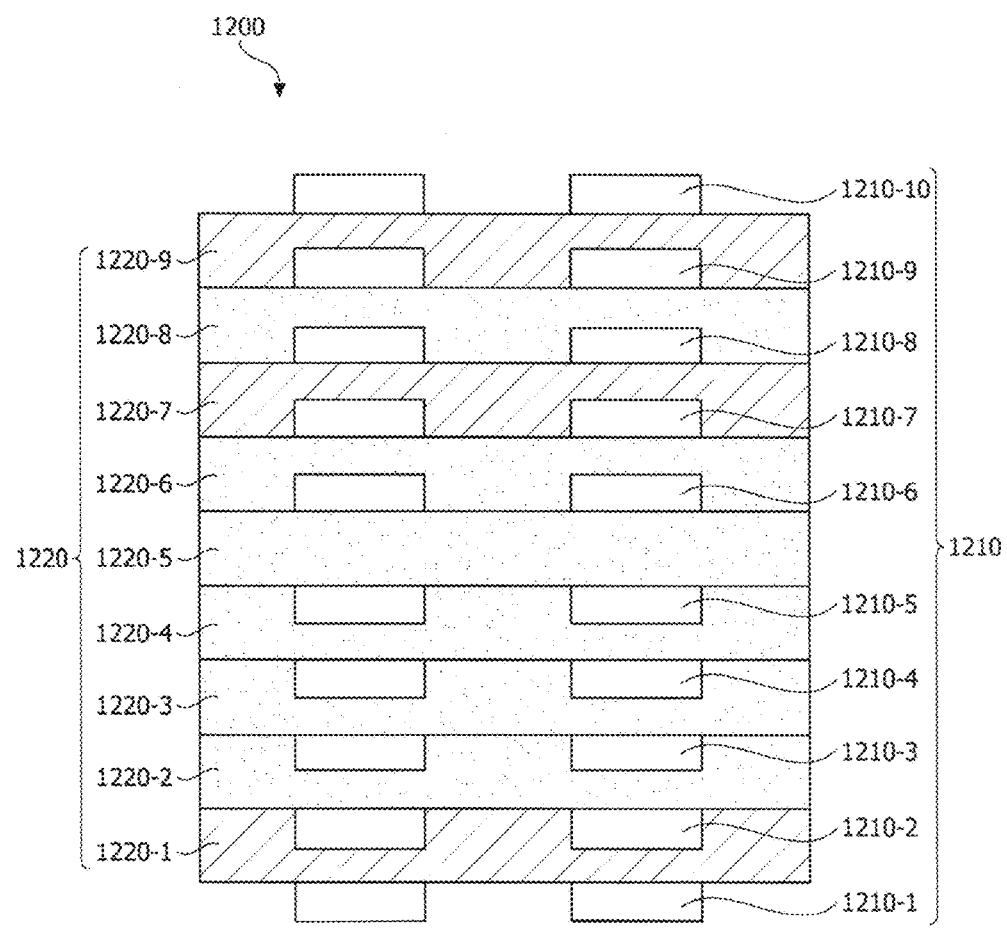
FIG. 11 is a cross-sectional view of a ten-layer printed circuit board according to another exemplary embodiment of the present invention.
Figure 12:
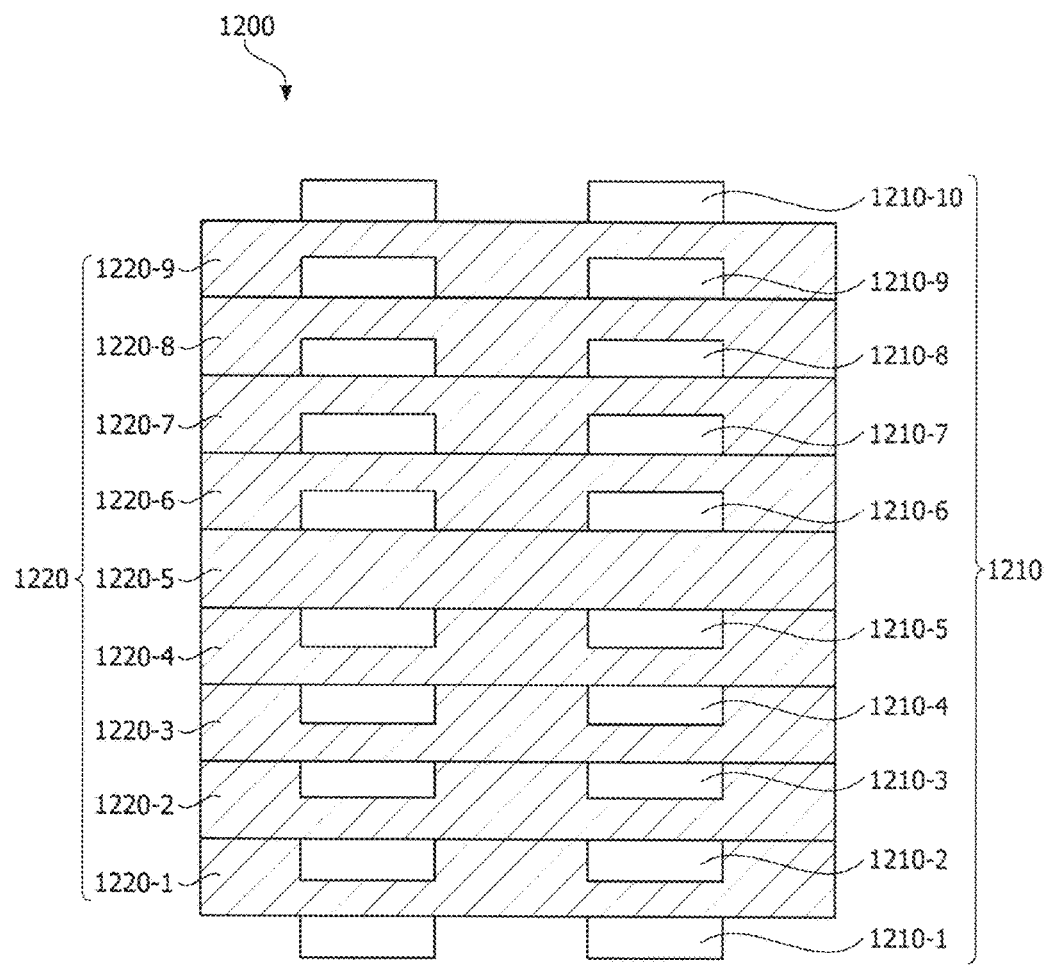
FIG. 12 is a cross-sectional view of ten-layer printed circuit board according to still another exemplary embodiment of the present invention.

FIG. 10 is a cross-sectional view of a ten-layer printed circuit board according to an exemplary embodiment of the present invention, FIG. 11 is a cross-sectional view of a ten-layer printed circuit board according to another exemplary embodiment of the present invention, and FIG. 12 is a cross-sectional view of a ten-layer printed circuit board according to still another exemplary embodiment of the present invention.

Referring to FIGS. 10 to 12, a ten-layer printed circuit board 1200 includes a plurality of circuit pattern layers 1210 sequentially disposed, and a plurality of insulating layers 1220 formed between the plurality of circuit pattern layers 1210.

For example, the plurality of circuit pattern layers 1210-1, . . . , 1210-10 are sequentially disposed, and the plurality of insulating layers 1220-1, . . . , 1220-9 may be formed between the plurality of circuit pattern layers 1210-1, . . . , 1210-10.

Referring to FIG. 10, at least one of an insulating layer 1220-1 between a circuit pattern layer 1210-1 and a circuit pattern layer 1210-2, which is the lowermost insulating layer 1220-1, and an insulating layer 1220-9 between a circuit pattern layer 1210-9 and a circuit pattern layer 1210-10, which is the uppermost insulating layer 1220-9 includes the epoxy resin composition according to an exemplary embodiment of the present invention.

Here, thicknesses of the insulating layers 1220-1 and 1220-9 including the epoxy resin composition may range from 30 μm to 1 mm. When the thicknesses of the insulating layers 1220-1 and 1220-9 satisfy the above-described numerical range, a decrease in surface temperature of the printed circuit board may be achieved.

Also, the insulating layers 1220-2, . . . , 1220-8 of the plurality of insulating layers may include an epoxy resin-containing glass fiber. Here, the epoxy resin may include an amorphous epoxy compound. The amorphous epoxy compound may be a conventional amorphous epoxy compound having two or more epoxy groups in a molecule, for example, a bisphenol A-type epoxy compound, a bisphenol F-type epoxy compound, a cyclic epoxy compound, a novolac-type epoxy compound, or an aliphatic epoxy compound.

The epoxy resin-containing glass fiber may include, for example, FR-4.

Referring to FIGS. 11 and 12, at least some of the remainder of the insulating layers 1220-2, . . . , 1220-8, except the lowermost insulating layer 1220-1 and the uppermost insulating layer 1220-9, may also include the epoxy resin composition according to an exemplary embodiment of the present invention.

Figure 13:
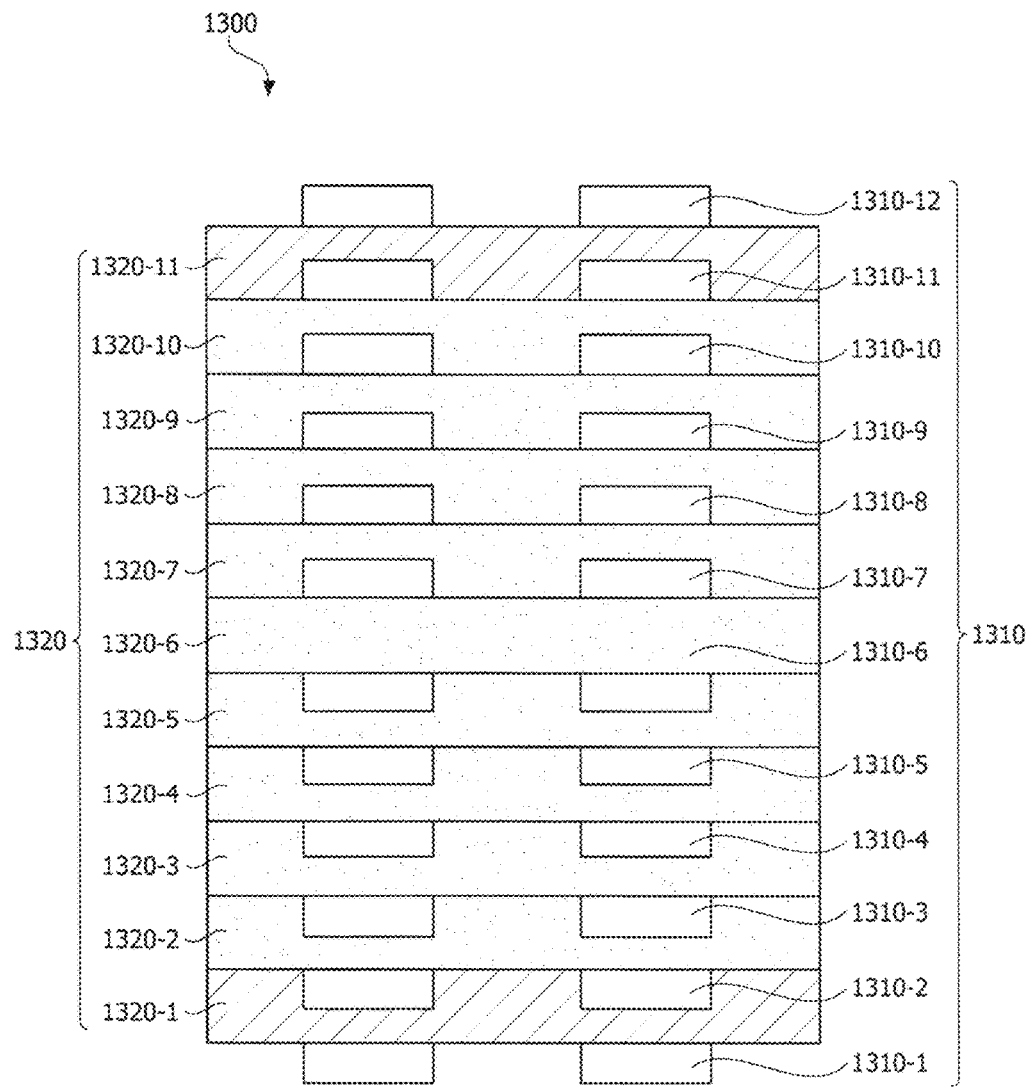
FIG. 13 is a cross-sectional view of a twelve-layer printed circuit board according to an exemplary embodiment of the present invention.

FIG. 13 is a cross-sectional view of a twelve-layer printed circuit board according to an exemplary embodiment of the present invention.

Referring to FIG. 13, a twelve-layer printed circuit board 1300 includes a plurality of circuit pattern layers 1310 sequentially disposed, and a plurality of insulating layers 1320 formed between the plurality of circuit pattern layers 1310.

For example, the plurality of circuit pattern layers 1310-1, . . . , 1310-12 may be sequentially disposed, and the plurality of insulating layers 1320-1, . . . , 1320-11 may be formed between the plurality of circuit pattern layers 1310-1, 1310-12.

Referring to FIG. 13, at least one of the insulating layer 1320-1 formed between the circuit pattern layer 1310-1 and the circuit pattern layer 1310-2, which is the lowermost insulating layer 1320-1, and the insulating layer 1320-11 formed between the circuit pattern layer 1310-11 and the circuit pattern layer 1310-12, which is the uppermost insulating layer 1320-11, includes the epoxy resin composition according to an exemplary embodiment of the present invention.

Here, the thicknesses of the insulating layers 1320-1 and 1320-11 including the epoxy resin composition may range from 30 μm to 1 mm. When the thicknesses of the insulating layers 1320-1 and 1320-11 satisfy the above-described numerical range, a decrease in surface temperature of the printed circuit board may be achieved.

Also, the insulating layers 1320-2, . . . , 1320-10 of the plurality of insulating layers may include an epoxy resin-containing glass fiber. Here, the epoxy resin may include an amorphous epoxy compound. The amorphous epoxy compound may be a conventional amorphous epoxy compound having two or more epoxy groups in a molecule, for example, a bisphenol A-type epoxy compound, a bisphenol F-type epoxy compound, a cyclic epoxy compound, a novolac-type epoxy compound, or an aliphatic epoxy compound.

The epoxy resin-containing glass fiber may include, for example, FR-4.

Although not illustrated in FIG. 13, at least some of the rest of the insulating layers 1320-2, . . . , 1320-10, except the lowermost insulating layer 1320-1 and the uppermost insulating layer 1320-11, may also include the epoxy resin composition according to an exemplary embodiment of the present invention.

The epoxy resin composition according to an exemplary embodiment of the present invention, which is included in the insulating layer of the printed circuit board, may be an epoxy resin composition including an epoxy compound and an inorganic filler, which includes a surface-modified boron nitride, on the surface of which a polycyclic aromatic hydrocarbon having a functional group is provided as described above.

Alternatively, the epoxy resin composition according to an exemplary embodiment of the present invention, which is included in the insulating layer of the printed circuit board, may be an epoxy resin composition according to a second exemplary embodiment. The epoxy resin composition according to the second exemplary embodiment may include a crystalline epoxy compound having a mesogen structure, a curing agent and an inorganic filler, wherein the content of the epoxy compound may be 7 to 66 wt %, preferably, 7.5 to 35 wt %, more preferably, 8 to 30 wt % with respect to the total epoxy resin composition. When the content of the epoxy compound is 7 to 66 wt % of the total epoxy resin composition, a satisfactory adhesive strength may be obtained, and the control of a thickness may be facilitated.

Here, the epoxy compound may include a crystalline epoxy compound having a mesogen structure. Here, the mesogen is the basic unit of a liquid crystal, and has a rigid structure. The mesogen may have, for example, rigid structures as shown in (a) to (e).

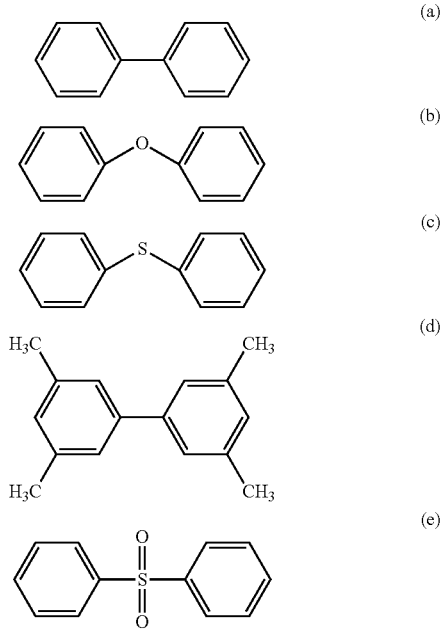

The crystalline epoxy compound having a mesogen structure may include, for example, 4,4'-biphenyl ether diglycidyl ether, that is, SE-4280.

Also, the epoxy compound may further include an amorphous epoxy compound.

The content of the crystalline epoxy compound having a mesogen structure may be 25 to 100 wt %, preferably, 45 to 90 wt %, and more preferably, 65 to 80 wt %, and the content of the amorphous epoxy compound may be 0 to 75 wt %, preferably, 10 to 55 wt %, and more preferably, 20 to 35 wt %, with respect to the total epoxy compound composition.

When the crystalline epoxy compound and the amorphous epoxy compound are included within the above-described numerical range, crystallization may be facilitated, thereby increasing a thermal conductive effect, and room temperature stabilization is possible. Here, the epoxy compound may include at least one type of crystalline epoxy compound having a mesogen structure.

The amorphous epoxy compound may be a conventional amorphous epoxy compound having two or more epoxy groups in a molecule.

The amorphous epoxy compound may be, for example, a glycidyl ether compound derived from one of bisphenol A, bisphenol F, 3,3',5,5'-tetramethyl-4,4'-dihydroxydiphenylmethane, 4,4'-dihydroxydiphenylsulfone, 4,4'-dihydroxydiphenylsulfide, 4,4'-dihydroxydiphenylketone, fluorene bisphenol, 4,4'-biphenol,3,3',5,5'-tetramethyl-4,4'-dihydroxybiphenyl, 2,2'-biphenol, resorcin, catechol, t-butylcatechol, hydroquinone, t-butylhydroquinone, 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,4-dihydroxynaphthalene, 2,5-dihydroxynaphthalene, 2,6-dihydroxynaphthalene, 2,7-dihydroxynaphthalene, 2,8-dihydroxynaphthalene, an allylated or polyallylated compound of the dihydroxynaphthalene, dihydric phenols including allylated bisphenol A, allylated bisphenol F, and allylated phenolnovolac, or trihydric or more phenols including phenol novolac, bisphenol A novolac, o-cresolnovolac, m-cresolnovolac, p-cresolnovolac, xylenolnovolac, poly-p-hydroxystyrene, tris-(4-hydroxyphenyl)methane, 1,1,2,2-tetrakis(4-hydroxyphenyl)ethane, fluoroglycinol, pyrogallol, t-butylpyrogallol, allylated pyrogallol, polyallylated pyrogallol, 1,2,4-benzenetriol, 2,3,4-trihydroxybenzophenone, a phenolaralkyl resin, a naphtolaralkyl resin, or a dicyclopentadiene-based resin, and halogenated bisphenols such as tetrabromobisphenol A, or a mixture selected therefrom.

The epoxy resin, composition according to an exemplary embodiment of the present invention may include a curing agent. The content of the curing agent may be 2 to 22 wt %® with respect to the total epoxy resin composition. When the content of the curing agent is 2 to 22 wt % of the total epoxy resin composition, a satisfactory adhesive strength may be obtained, and the control of a thickness may be facilitated. The epoxy resin composition may include at least one of an amine-based curing agent, a phenol-based curing agent, an acid anhydride-based curing agent, a polymercaptan-based curing, agent, a polyaminoamide-based curing agent, an isocyanate-based curing agent, and a block isocyanate-based curing agent.

The amine-based curing agent may be, for example, 4, 4'-diaminodiphenylsulfone.

Another example of the amine-based curing agent may include aliphatic amines, polyetherpolyamines, alicyclic amines, and aromatic amines. As the aliphatic amine, ethylenediamine, 1,3-diaminopropane, 1,4-diaminopropane, hexamethylenediamine, 2,5-dimethylhexamethylenediamine, trimethylhexamethylenediamine, diethylenetriamine, iminobispropylamine, bis(hexamethylene)triamine, triethylenetetramine, tetraethylene pentamine, pentaethylenehexamine, N-hydroxyethylethylenediamine, or tetra(hydroxyethypethylenediamine may be used. The polyethelpolyamine may be one of triethyleneglycoldiamine, tetraethyleneglycoldiamine, diethyleneglycolbis(propylamine), polyoxypropylenediamine, polyoxypropylenetriamine and a mixture selected therefrom. The alicyclic amine may be isophorone diamine, metacene diamine, N-aminoethylpiperazine, bis(4-amino-3-methyldicyclohexyl)methane, bis(aminomethyl)cyclohexane, 3,9-bis(3-aminopropyl)2,4,8,10-tetraoxaspiro(5,5)undecane, or norbornene diamine may be used. The aromatic amine may be one of tetrachloro-p-xylenediamine, m-xylenediamine, p-xylenediamine, m-phenylenediamine, o-phenylenediamine, p-phenylenediamine, 2,4-diaminoanisole, 2,4-toluenediamine, 2,4-diaminodiphenylmethane, 4,4'-diaminodiphenylmethane, 4,4'-diamino-1,2-diphenylethane, 2,4-diaminodiphenylsulfone, m-aminophenol, m-aminobenzylamine, benzyldimethylamine, 2-dimethyl aminomethyl)phenol, triethanolamine, methylbenzylamine, α-(m-aminophenyl)ethylamine, α-(p-aminophenyl)ethylamine, diaminodiethyldimethyldiphenylmethane, α,α'-bis(4-aminophenyl)-p-diisopropylbenzene, and a mixture selected therefrom.

The phenol-based curing agent may be, for example, one of bisphenol A, bisphenol F, 4,4'-dihydroxydiphenylmethane, 4,4'-dihydroxydiphenylether, 1,4-bis(4-hydroxyphenoxy)benzene, 1,3-bis(4-hydroxyphenoxy)benzene, 4,4'-dihydroxydiphenylsulfide, 4,4'-dihydroxydiphenylketone, 4,4'-dihydroxydiphenylsulfone, 4,4'-dihydroxydiphenylester, 4,4'-dihydroxybiphenyl, 2,2'-dihydroxybiphenyl, 10-(2,5-dihydroxyphenyl)-10H-9-oxa-10-phosphaphenantrene-10-oxide, phenolnovolac, bisphenolAnovolac, o-cresolnovolac, m-cresolnovolac, p-cresolnovolac, xylenolnovolac, poly-p-hydroxystyrene, hydroquinone, resorcin, catechol, t-butylcatechol, t-butylhydroquinone, fluoroglycinol, pyrogallol, t-butylpyrogallol, allylated pyrogallol, polyallylated pyrogallol, 1,2,4-benzenetriol, 2,3,4-trihydroxybenzophenone, 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,4-dihydroxynaphthalene, 2,5-dihydroxynaphthalene, 2,6-dihydroxynaphthalene, 2,7-dihydroxynaphthalene, 2,8-dihydroxynaphthalene, an allylated or polyallylated compound of the dihydroxynaphthalene, allylated bisphenol A, allylated bisphenol F, allylated phenolnovolac, allylated pyrogallol, and a mixture selected therefrom.

The acid anhydride-based curing agent may be, for example, one of dodecenyl succinic anhydride, poly(adipic anhydride), poly(azelaic anhydride), poly(sebacic anhydride), poly(ethyloctadecanedioic)anhydride, poly(phenylhexadecanedioic)anhydride, methyltetrahydrophthalic anhydride, methylhexahydrophthalic anhydride, hexahydrophthalic anhydride, methyl himic anhydride, tetrahydrophthalic anhydride, trialkyl tetrahydrophthalic anhydride, methylcyclohexene dicarboxylic anhydride, methylcyclohexene tetracarboxylic anhydride, phthalic anhydride, trimellitic anhydride, pyromellitic anhydride, benzophenone tetracarboxylic anhydride, ethylene glycol bis(trimellitate) anhydride, HET anhydride, nadic anhydride, methyl nadic anhydride, 5-(2,5-dioxotetrahydro-3-furanyl)-3-methyl-3-cyclohexane-1,2-dicarboxylic anhydride, 3,4-dicarboxy-1,2,3,4-tetrahydro-1-naphthalenesuccinic dianhydride, 1-methyl-dicarboxy-1,2,3,4-tetrahydro-1-naphthalenesuccinic dianhydride, and a mixture selected therefrom.

A combination of two or more types of the above-described curing agents may be used.

The epoxy resin composition according to an exemplary embodiment of the present invention may further include a curing accelerator. The curing accelerator may be, for example, an amine-based curing accelerator, an imidazole-based curing accelerator, an organic phosphine-based curing accelerator, or a Lewis acid curing accelerator, and specifically, a tertiary amine such as 1,8-diazabicyclo(5,4,0)undecene-7, triethylenediamine, benzyldimethylamine, triethanolamine, dimethylaminoethanol or tris(dimethylaminomethyl)phenol, an imidazole such as 2-methylimidazole, 2-phenylimidazole, 2-phenyl-4-methylimidazole or 2-heptadecylimidazole, an organic phosphine such as tributylphosphine, methyldiphenylphosphine, triphenylphosphine, diphenylphospine, or phenylphosphine, a tetra-substituted phosphonium-tetra-substituted borate such as tetraphenyl phosphonium tetraphenyl borate, tetraphenyl phosphonium ethyltriphenyl borate, and tetrabutyl phosphonium tetrabutyl borate; or a tetraphenyl boron salt such as 2-ethyl-4-methylimidazole-tetraphenyl borate or N-methylmorpholine tetraphenyl borate.

The epoxy resin composition according to the second exemplary embodiment may include 17 to 90 wt % of an inorganic filler with respect to the total epoxy resin composition. When the content of the inorganic filler is 17 to 90 wt %, the high thermal conductive property, low thermal expansion property and high temperature thermal resistance of the epoxy resin composition may be improved. As the content of the inorganic filler is increased, the high thermal conductive property, low thermal expansion property and high temperature thermal resistance are improved. However, these properties are not improved by the volume fraction of the inorganic filler, and are dramatically improved with a specific content of the inorganic filler. On the other hand, when the content of the inorganic filler is more than 90 wt %, viscosity is increased, and thus moldability is degraded.

According to the second exemplary embodiment, the inorganic filler may include at least one of alumina, boron nitride, aluminum nitride, silicon carbide, crystalline silica, barium sulfate, carbon black, polymethylsilsesquioxane (PMSSO) and a mixture selected therefrom.

Hereinafter, according to an exemplary embodiment of the present invention, the comparison results of heat dissipating performance between a printed circuit board in which some insulating layers include the epoxy resin composition according to the second exemplary embodiment, and a printed circuit board in which all of the insulating layers include FR-4 will be described.

Hereinafter, an epoxy resin composition included in an insulating layer of Examples 2-1 to 2-5 is a composition including 6.6 wt % of a crystalline epoxy compound having a mesogen structure, 2.2 wt % of a bisphenol A-type amorphous epoxy compound, 3.2 wt % of diaminodiphenylsulfone, and 88 wt % of alumina, and has a thermal conductivity of 10.03 w/mK.

Thermal stress was applied 10 cycles by floating the printed circuit boards according to examples and comparative examples on 288° C. solder for 10 seconds per each cycle. Here, the cycles at which the circuit pattern layer and the insulating layer are separated from each other, or a pore starts swelling were recorded.

An elevated temperature is a result obtained by attaching a ceramic-based heat source on which a thermocouple is fixed to the printed circuit boards according to the examples and comparative examples and measuring a temperature of the heat source at room temperature (25° C.). The same output (voltage×ampere) was applied to the printed circuit boards according to the examples and comparative examples, followed by measuring a temperature. The result obtained by subtracting the temperature measured at room temperature from the temperature measured after the application of the output was determined as an elevated temperature.

Table 4 shows the comparison results of heat dissipating performance between the four-layer printed circuit boards shown in FIGS. 8 and 9.

TABLE 4

|  | Exemplary embodiment 2-1 | | Comparative Example 2-1 | |
|---|---|---|---|---|
| Cross-sectional structure | Type | Thickness [mm] | Type | Thickness [mm] |
| Circuit pattern layer (1110-4) | Cu | 0.033 | Cu | 0.033 |
| Insulating layer (1120-3) | Epoxy resin composition | 0.11 | FR-4 | 0.085 |
| Circuit pattern layer (1110-3) | Cu | 0.033 | Cu | 0.033 |
| Insulating layer (1120-1) | FR-4 | 0.2 | FR-4 | 0.2 |
| Circuit pattern layer (1110-2) | Cu | 0.033 | Cu | 0.033 |
| Insulating layer (1120-1) | Epoxy resin composition | 0.11 | FR-4 | 0.085 |
| Circuit pattern layer (1110-1) | Cu | 0.033 | Cu | 0.033 |
| Thermal stress | 10 cycles | | 10 cycles | |
| Elevated temperature (° C.) | 53.0 | | 60.7 | |

Referring to Table 4, it can be seen that the four-layer printed circuit boards of Example 2-1 and Comparative Example 2-1 can resist 10 cycles of thermal stress. Also, compared to Comparative Example 2-1 in which all of the insulating layers include FR-4 (elevated temperature: 60.7° C.), the elevated temperature of the Example 2-1 in which the lower insulating layer 1120-1 and the upper insulating layer 1120-3 include an epoxy resin composition (elevated temperature: 53.0° C.) is low. Accordingly, it is concluded that the printed circuit board of Example 2-1 has an excellent heat dissipating performance, compared to that of Comparative Example 2-1.

Below, Table 5 shows the comparison results of heat dissipating performance between the 10-layer printed circuit boards shown in FIGS. 10 to 12.

TABLE 5

| Cross-sectional structure | Example 2-2 | | Example 2-3 | | Example 2-4 | | Comparative Example 2-2 | |
|---|---|---|---|---|---|---|---|---|
|  | Type | Thickness [mm] | Type | Thickness [mm] | Type | Thickness [mm] | Type | Thickness [mm] |
| Circuit pattern layer (1210-10) | Cu | 0.025 | Cu | 0.025 | Cu | 0.025 | Cu | 0.025 |
| Insulating layer (1220-9) | Epoxy resin composition | 0.075 | Epoxy resin composition | 0.075 | Epoxy resin composition | 0.075 | FR-4 | 0.060 |
| Circuit pattern layer (1210-9) | Cu | 0.020 | Cu | 0.020 | Cu | 0.025 | Cu | 0.020 |
| Insulating layer (1220-8) | FR-4 | 0.060 | Epoxy resin composition | 0.075 | Epoxy resin composition | 0.075 | FR-4 | 0.060 |
| Circuit pattern layer (1210-8) | Cu | 0.020 | Cu | 0.020 | Cu | 0.025 | Cu | 0.020 |
| Insulating layer (1220-7) | FR-4 | 0.060 | FR-4 | 0.060 | Epoxy resin composition | 0.075 | FR-4 | 0.060 |
| Circuit pattern layer (1210-7) | Cu | 0.020 | Cu | 0.020 | Cu | 0.025 | Cu | 0.020 |
| Insulating layer (1220-6) | FR-4 | 0.060 | FR-4 | 0.060 | Epoxy resin composition | 0.075 | FR-4 | 0.060 |
| Circuit pattern layer (1210-6) | Cu | 0.020 | Cu | 0.020 | Cu | 0.025 | Cu | 0.020 |
| Insulating layer (1220-5) | FR-4 | 0.060 | FR-4 | 0.060 | Epoxy resin composition | 0.075 | FR-4 | 0.060 |

TABLE 5-continued

| Cross-sectional structure | Example 2-2 Type | Thickness [mm] | Example 2-3 Type | Thickness [mm] | Example 2-4 Type | Thickness [mm] | Comparative Example 2-2 Type | Thickness [mm] |
|---|---|---|---|---|---|---|---|---|
| Circuit pattern layer (1210-5) | Cu | 0.020 | Cu | 0.020 | Cu | 0.025 | Cu | 0.020 |
| Insulating layer (1220-4) | FR-4 | 0.060 | FR-4 | 0.060 | Epoxy resin composition | 0.075 | FR-4 | 0.060 |
| Circuit pattern layer (1210-4) | Cu | 0.020 | Cu | 0.020 | Cu | 0.025 | Cu | 0.020 |
| Insulating layer (1220-3) | FR-4 | 0.060 | FR-4 | 0.060 | Epoxy resin composition | 0.075 | FR-4 | 0.060 |
| Circuit pattern layer (1210-3) | Cu | 0.020 | Cu | 0.020 | Cu | 0.025 | Cu | 0.020 |
| Insulating layer (1220-2) | FR-4 | 0.060 | FR-4 | 0.060 | Epoxy resin composition | 0.075 | FR-4 | 0.060 |
| Circuit pattern layer (1210-2) | Cu | 0.020 | Cu | 0.020 | Cu | 0.025 | Cu | 0.020 |
| Insulating layer (1220-1) | Epoxy resin composition | 0.075 | Epoxy resin composition | 0.075 | Epoxy resin composition | 0.075 | FR-4 | 0.060 |
| Circuit pattern layer (1210-1) | Cu | 0.025 | Cu | 0.025 | Cu | 0.025 | Cu | 0.025 |
| Thermal stress | 10 cycles | | 10 cycles | | 10 cycles | | 10 cycles | |
| Elevated temperature (° C.) | 62.6 | | 60.7 | | 51.7 | | 70.1 | |

As shown in Table 5, it can be seen that the ten-layer printed circuit boards of Examples 2-2 to 2-4 and Comparative Example 2-2 also resist all of 10 cycles of thermal stress. Also, compared to Comparative Example 2-2 in which all of the insulating layers include FR-4 (elevated temperature: 70.1° C.), the elevated temperatures of Examples 2-2, 2-3 and 2-4 in which all or some of the insulating layers include an epoxy resin composition are low. As a result, it is concluded that the printed circuit boards of Examples 2-2 to 2-4 exhibit excellent heat dissipating performance, compared to that of Comparative Example 2-2.

Below, Table 6 shows the comparison results of heat dissipating performance of the twelve-layer printed circuit board shown in FIG. 13.

TABLE 6

| Cross-sectional structure | Example 2-5 Type | Thickness [mm] | Comparative Example 2-3 Type | Thickness [mm] |
|---|---|---|---|---|
| Circuit pattern layer (1310-12) | Cu | 0.025 | Cu | 0.025 |
| Insulating layer (1320-11) | Epoxy resin composition | 0.075 | FR-4 | 0.035 |
| Circuit pattern layer (1310-11) | Cu | 0.015 | Cu | 0.015 |
| Insulating layer (1320-10) | FR-4 | 0.035 | FR-4 | 0.035 |
| Circuit pattern layer (1310-10) | Cu | 0.015 | Cu | 0.015 |
| Insulating layer (1320-9) | FR-4 | 0.035 | FR-4 | 0.035 |
| Circuit pattern layer (1310-9) | Cu | 0.015 | Cu | 0.015 |
| Insulating layer (1320-8) | FR-4 | 0.035 | FR-4 | 0.035 |
| Circuit pattern layer (1310-8) | Cu | 0.015 | Cu | 0.015 |
| Insulating layer (1320-7) | FR-4 | 0.045 | FR-4 | 0.045 |
| Circuit pattern layer (1310-7) | Cu | 0.020 | Cu | 0.020 |
| Insulating layer (1320-6) | FR-4 | 0.060 | FR-4 | 0.060 |
| Circuit pattern layer (1310-6) | Cu | 0.020 | Cu | 0.020 |
| Insulating layer(1320-5) | FR-4 | 0.045 | FR-4 | 0.045 |
| Circuit pattern layer (1310-5) | Cu | 0.015 | Cu | 0.015 |
| Insulating layer (1320-4) | FR-4 | 0.035 | FR-4 | 0.035 |

TABLE 6-continued

|  | Example 2-5 | | Comparative Example 2-3 | |
|---|---|---|---|---|
| Cross-sectional structure | Type | Thickness [mm] | Type | Thickness Thickness [mm] |
| Circuit pattern layer (1310-4) | Cu | 0.015 | Cu | 0.015 |
| Insulating layer (1320-3) | FR-4 | 0.035 | FR-4 | 0.035 |
| Circuit pattern layer (1310-3) | Cu | 0.015 | Cu | 0.015 |
| Insulating layer (1320-2) | FR-4 | 0.035 | FR-4 | 0.035 |
| Circuit pattern layer(1310-2) | Cu | 0.015 | Cu | 0.015 |
| Insulating layer (1320-1) | Epoxy resin composition | 0.035 | FR-4 | 0.035 |
| Circuit pattern layer (1310-1) | Cu | 0.025 | Cu | 0.025 |
| Thermal stress | 10 cycles | | 10 cycles | |
| Elevated temperature (° C.) | 66.8 | | 74.0 | |

As shown in Table 6, it can be seen that the twelve-layer printed circuit boards of Example 2-5 and Comparative Example 2-3 resist all of 10 cycles of thermal stress. Also, compared to Comparative Example 2-3 in which all of the insulating layers include FR-4 (elevated temperature: 74.0° C.), the elevated temperature of Example 2-5 in which all or some of the insulating layers include an epoxy resin composition (elevated temperature: 66.8° C.) is low. As a result, it is concluded that the printed circuit board of Example 2-5 exhibits excellent heat dissipating performance, compared to that of Comparative Example 2-3.

As described above, it can be seen that when at least some of the insulating layers include an epoxy resin composition, which includes a crystalline epoxy compound having a mesogen structure, a curing agent and an inorganic filler, in a multi-layer printed circuit board, the printed circuit board exhibits excellent heat dissipating performance.

Also, the epoxy resin composition included in the insulating layer of the printed circuit board according to an exemplary embodiment of the present invention may be an epoxy resin composition according to a third exemplary embodiment.

The epoxy resin composition according to the third exemplary embodiment may be an epoxy resin composition, which includes an epoxy compound including a crystalline epoxy compound, a curing agent and an inorganic filler including glass fiber.

The epoxy resin composition according to the third exemplary embodiment includes 3 to 60 wt % of the epoxy compound including a crystalline epoxy compound, 0.5 to 22 wt % of the curing agent, and 18 to 96.5 wt % of the inorganic filler including glass fiber.

When 3 to 60 wt % of the epoxy compound is included in the epoxy resin composition according to the third exemplary embodiment, due to a satisfactory hardness, an excellent adhesive strength is obtained, and the control of a thickness is facilitated. Also, when 0.5 to 22 wt % of the curing agent is included in the epoxy resin composition according to the third exemplary embodiment, curing is facilitated, and a satisfactory hardness and an excellent adhesive strength are obtained. Also, when 18 to 96.5 wt % of the inorganic filler including glass fiber is included in the epoxy resin composition according to the third exemplary embodiment, an excellent thermal conductivity and a low electrical conductivity are obtained, and a low temperature expansion property, a high thermal resistance and excellent moldability are obtained.

The epoxy resin composition according to the third exemplary embodiment may further include an amorphous epoxy compound. The content of the amorphous epoxy compound may be 1 to 40 parts by weight with respect to 10 parts by weight of the crystalline epoxy compound. When the crystalline epoxy compound and the amorphous epoxy compound are included at the above-described ratio, room temperature stability may be increased.

Also, the curing agent included in the epoxy resin composition according to the third exemplary embodiment may include at least one of an amine-based curing agent, a phenol-based curing agent, an acid anhydride-based curing agent, a polymercaptan-based curing agent, a polyaminoamide-based curing agent, an isocyanate-based curing agent and a block isocyanate-based curing agent.

Also, the epoxy resin composition according to the third exemplary embodiment includes 18 to 96.5 wt % of the inorganic filler including glass fiber. When the inorganic filler including glass fiber is included at the same content as described above, an epoxy resin composition having a low dielectric constant and an excellent thermal conductivity may be obtained.

Here, the content of glass fiber may be 25 to 55 wt %, and preferably, 30 to 50 wt % of the total epoxy resin composition. When the content of the glass fiber is less than 25 wt %, due to a low dielectric constant, it is difficult to be used for an insulating layer. When the content of the glass fiber is more than 55 wt %, a desired level of thermal conductivity may not be obtained, and processing may be difficult to perform.

Meanwhile, the epoxy resin composition according to the third exemplary embodiment may further include at least one of boron nitride and alumina as the inorganic filler. Here, the content of at least one of the boron nitride and the alumina may be 1 to 25 wt %, preferably, 5 to 25 wt %, and more preferably, 10 to 20 wt % of the total epoxy resin composition. Here, the content may refer to the content of the boron nitride or alumina when the epoxy resin composition includes the boron nitride or alumina, and refer to the content of the boron nitride and the alumina when the epoxy resin composition includes the boron nitride and the alumina. When the content of at least one of the boron nitride and the alumina is less than 1 wt % of the total epoxy resin composition, it is difficult to obtain a desired level of thermal conductivity. When the content of at least one of the boron nitride and the alumina is more than 25 wt % of the total epoxy resin composition, a dielectric constant is increased.

Here, 3 to 7 parts by weight of the boron nitride may be included with respect to 10 parts by weight of the glass fiber, and 3 to 5 parts by weight of the alumina may be further included with respect to 10 parts by weight of the glass fiber. When the glass fiber, the boron nitride and the alumina are included within the above-described numerical range, an epoxy resin composition having a high thermal conductivity and a satisfactory dielectric constant may be obtained.

Also, the epoxy resin composition according to the third exemplary embodiment may further include at least one of aluminum nitride and silica as the inorganic filler.

Hereinafter, the present invention will be described in further detail with reference to examples and comparative examples.

Example 3-1

35 wt % of a crystalline epoxy compound (4,4'-biphenyl ether diglycidyl ether), 12.5 wt % of 4,4'-diaminophenylsulfone and 2.5 wt % of a curing accelerator were dissolved in MEK for 20 minutes, 50 wt % of glass fiber was added, and then the resulting solution was stirred for 2 hours. After the stirring, a copper plate was coated with the resulting solution, and pressurized at 150° C. for 1.5 hours, thereby obtaining an epoxy resin composition of Example 3-1.

Example 3-2

35 wt % of a crystalline epoxy compound (4,4'-biphenyl ether diglycidyl ether), 12.5 wt % of 4,4'-diaminophenylsulfone and 2.5 wt % of a curing accelerator were dissolved in MEK for 20 minutes, 40 wt % of glass fiber and 10 wt % of boron nitride were added, and then the resulting solution was stirred for 2 hours. After the stirring, a copper plate was coated with the resulting solution, and pressurized at 150° C. for 1.5 hours, thereby obtaining an epoxy resin composition of Example 3-2.

Example 3-3

20 wt % of a crystalline epoxy compound (4,4'-biphenyl ether diglycidyl ether), 15 wt % of the amorphous epoxy compound of Formula 4, 12.5 wt % of 4,4'-diaminophenylsulfone and 2.5 wt % of a curing accelerator were dissolved in MEK for 20 minutes, 40 wt % of glass fiber and 10 wt % of boron nitride were added, and then the resulting solution was stirred for 2 hours. After the stirring, a copper plate was coated with the resulting solution, and pressurized at 150° C. for 1.5 hours, thereby obtaining an epoxy resin composition of Example 3-3.

Example 3-4

30 wt % of a crystalline epoxy compound (4,4'-biphenyl ether diglycidyl ether), 5 wt % of the amorphous epoxy compound of Formula 4, 12.5 wt % of 4,4'-diaminophenylsulfone and 2.5 wt % of a curing accelerator were dissolved in MEK for 20 minutes, 40 wt % of glass fiber and 10 wt % of boron nitride were added, and then the resulting solution was stirred for 2 hours. After the stirring, a copper plate was coated with the resulting solution, and pressurized at 150° C. for 1.5 hours, thereby obtaining an epoxy resin composition of Example 3-4.

Example 3-5

35 wt % of a crystalline epoxy compound (4,4'-biphenyl ether diglycidyl ether), 12.5 wt % of 4,4'-diaminophenylsulfone and 2.5 wt % of a curing accelerator were dissolved in MEK for 20 minutes, 40 wt % of glass fiber and 10 wt % of alumina were added, and then the resulting solution was stirred for 2 hours. After the stirring, a copper plate was coated with the resulting solution, and pressurized at 150° C. for 1.5 hours, thereby obtaining an epoxy resin composition of Example 3-5.

Example 3-6

35 wt % of a crystalline epoxy compound (4,4'-biphenyl ether diglycidyl ether), 12.5 wt % of 4,4'-diaminophenylsulfone and 2.5 wt % of a curing accelerator were dissolved in MEK for 20 minutes, 30 wt % of glass fiber and 20 wt % of alumina were added, and then the resulting solution was stirred for 2 hours. After the stirring, a copper plate was coated with the resulting solution, and pressurized at 150° C. for 1.5 hours, thereby obtaining an epoxy resin composition of Example 3-6.

Example 3-7

35 wt % of a crystalline epoxy compound (4,4'-biphenyl ether diglycidyl ether), 12.5 wt % of 4,4'-diaminophenylsulfone and 2.5 wt % of a curing accelerator were dissolved in MEK for 20 minutes, 30 wt % of glass fiber and 20 wt % of alumina were added, and then the resulting solution was stirred for 2 hours. After the stirring, a copper plate was coated with the resulting solution, and pressurized at 150° C. for 1.5 hours, thereby obtaining an epoxy resin composition of Example 3-7.

Example 3-8

35 wt % of a crystalline epoxy compound (4,4'-biphenyl ether diglycidyl ether), 12.5 wt % of 4,4'-diaminophenylsulfone and 2.5 wt % of a curing accelerator were dissolved in MEK for 20 minutes, 30 wt % of glass fiber and 10 wt % of alumina were added, and then the resulting solution was stirred for 2 hours. After the stirring, a copper plate was coated with the resulting solution, and pressurized at 150° C. for 1.5 hours, thereby obtaining an epoxy resin composition of Example 3-8.

Comparative Example 3-1

35 wt % of an amorphous epoxy compound of Formula 4, 12.5 wt % of 4,4'-diaminophenylsulfone and 2.5 wt % of a curing accelerator were dissolved in MEK for 20 minutes, 50 wt % of glass fiber was added, and then the resulting solution was stirred for 2 hours. After the stirring, a copper plate was coated with the resulting solution, and pressurized at 150° C. for 1.5 hours, thereby obtaining an epoxy resin composition of Comparative Example 3-1.

Comparative Example 3-2

35 wt % of an amorphous epoxy compound of Formula 4, 12.5 wt % of 4,4'-diaminophenylsulfone and 2.5 wt % of a curing accelerator were dissolved in MEK for 20 minutes, 30 wt % of glass fiber, 10 wt % of boron nitride, and 10 wt % of alumina were added, and then the resulting solution was stirred for 2 hours. After the stirring, a copper plate was coated with the resulting solution, and pressurized at 150° C. for 1.5 hours, thereby obtaining an epoxy resin composition of Comparative Example 3-2.

Comparative Example 3-3

35 wt % of a crystalline epoxy compound (4,4'-biphenyl ether diglycidyl ether), 12.5 wt % of 4,4'-diaminophenylsulfone and 2.5 wt % of a curing accelerator were dissolved in MEK for 20 minutes, 50 wt % of alumina was added, and then the resulting solution was stirred for 2 hours. After the stirring, a copper plate was coated with the resulting solution, and pressurized at 150° C. for 1.5 hours, thereby obtaining an epoxy resin composition of Comparative Example 3-3.

Comparative Example 3-4

35 wt % of a crystalline epoxy compound (4,4'-biphenyl ether diglycidyl ether), 12.5 wt % of 4,4'-diaminophenylsulfone and 2.5 wt % of a curing accelerator were dissolved in MEK for 20 minutes, 20 wt % of glass fiber, 15 wt % of boron nitride and 15 wt % of alumina were added, and then the resulting solution was stirred for 2 hours. After the stirring, a copper plate was coated with the resulting solution, and pressurized at 150° C. for 1.5 hours, thereby obtaining an epoxy resin composition of Comparative Example 3-4.

Comparative Example 3-5

25 wt % of a crystalline epoxy compound (4,4'-biphenyl ether diglycidyl ether), 12.5 wt % of 4,4'-diaminophenylsulfone and 2.5 wt % of a curing accelerator were dissolved in MEK for 20 minutes, 60 wt % of glass fiber was added, and then the resulting solution was stirred for 2 hours. After the stirring, a copper plate was coated with the resulting solution, and pressurized at 150° C. for 1.5 hours, thereby obtaining an epoxy resin composition of Comparative Example 3-5.

Experimental Example

After the compositions obtained from Examples 3-1 to 3-8 and Comparative Examples 3-1 to 3-3 were cured, thermal conductivity was measured by a transient hot wire method using a LFA447-type thermal conductivity meter manufactured by NETZSCH, and a dielectric constant was measured by an RF/IV technique using an E4991A RF impedance/material analyzer manufactured by Agilent Technologies.

Tables 7 to 9 show the comparison results of a thermal conductivity and a dielectric constant between examples and comparative examples.

TABLE 7

| Experiment No. | Vertical thermal conductivity (w/mK) | Horizontal thermal conductivity (w/mK) | Dielectric constant |
|---|---|---|---|
| Example 3-1 | 2.234 | 2.343 | 3.68 |
| Comparative Example 3-1 | 0.443 | 0.502 | 3.50 |

TABLE 8

| Experiment No. | Vertical thermal conductivity (w/mK) | Horizontal thermal conductivity (w/mK) | Dielectric constant |
|---|---|---|---|
| Example 3-8 | 5.231 | 5.926 | 4.18 |
| Comparative Example 3-2 | 2.63 | 2.71 | 4.14 |

TABLE 9

| Experiment No. | Horizontal thermal conductivity (w/mK) | Horizontal thermal conductivity (w/mK) | Dielectric constant |
|---|---|---|---|
| Example 3-1 | 2.234 | 2.343 | 3.68 |
| Example 3-2 | 4.002 | 4.536 | 3.80 |
| Example 3-3 | 3.142 | 3.277 | 3.71 |
| Example 3-4 | 3.403 | 3.851 | 3.78 |
| Example 3-5 | 3.643 | 3.825 | 4.54 |
| Example 3-6 | 5.013 | 5.316 | 4.11 |
| Example 3-7 | 3.824 | 4.002 | 4.73 |
| Example 3-8 | 5.231 | 5.926 | 4.18 |
| Comparative Example 3-3 | 5.831 | 5.937 | 5.58 |

TABLE 9-continued

| Experiment No. | Horizontal thermal conductivity (w/mK) | Horizontal thermal conductivity (w/mK) | Dielectric constant |
|---|---|---|---|
| Comparative Example 3-4 | 5.456 | 6.002 | 5.12 |
| Comparative Example 3-5 | 0.762 | 0.931 | 3.62 |

Referring to Table 7, it can be seen that the epoxy resin composition of Example 3-1 including the crystalline epoxy compound, the curing agent and the glass fiber as the inorganic filler has a similar dielectric constant, but a higher thermal conductivity than the epoxy resin composition of Comparative Example 3-1 including the amorphous epoxy compound, the curing agent and the glass fiber as the inorganic filler at the same content ratio as that of Example 3-1.

Referring to Table 8, it can be seen that the epoxy resin composition of Example 3-8 including the crystalline epoxy compound, the curing agent and the glass fiber as the inorganic filler has a similar dielectric constant, but a higher thermal conductivity than the epoxy resin composition of Comparative Example 3-2 including the amorphous epoxy compound, the curing agent and the glass fiber as the inorganic filler at the same content ratio as that of Example 3-8.

Also, referring to Table 9, it can be seen that the epoxy resin compositions of Examples 3-1 to 3-8 including the glass fiber as the inorganic filler have a commercially available range of dielectric constant (less than 5). It can be seen that the epoxy resin composition of Comparative Example 3-3 without the glass fiber as the inorganic filler has a higher thermal conductivity than the epoxy resin compositions of Example 3-1 to 3-8, but has a dielectric constant (5.58) beyond the commercially available range, and thus the epoxy resin composition of Comparative Example 3-3 is not suitable to be used for an insulating layer. Also, it can be seen that the epoxy resin composition of Comparative Example 3-4 in which the content of the glass fiber is less than 25 wt % of the epoxy resin composition has a dielectric constant (5.12) beyond the commercially available range, and thus is not suitable to be used for an insulating layer. It can be seen that the epoxy resin composition of Comparative Example 3-5 in which the content of the glass fiber is more than 55 wt % of the epoxy resin composition has a dielectric constant (3.62) in a commercially available range, but has a low thermal conductivity.

Continuing to refer to Table 9, it can be seen that, compared to the epoxy resin composition of Example 3-1 including only the glass fiber as the inorganic filler, the epoxy resin compositions of Examples 3-2 to 3-8 further including boron nitride and/or alumina have a higher thermal conductivity. Also, it can be seen that the epoxy resin composition of Example 3-6 including 3 to 7 parts by weight of the boron nitride and the epoxy resin composition of Example 3-8 further including 3 to 5 parts by weight of the alumina, with respect to 10 parts by weight of the glass fiber, have similar dielectric constants, but have higher thermal conductivities, compared to the epoxy resin compositions of Examples 3-2 to 3-5 and 3-7.

Alternatively, the epoxy resin composition included in an insulating layer of a printed circuit board according to an exemplary embodiment of the present invention may be an epoxy resin composition according to a fourth exemplary embodiment.

The epoxy resin composition according to the fourth exemplary embodiment includes a dicyclopentadiene (DCPD)-type epoxy compound, a curing agent and an inorganic filler including planar boron nitride.

The content of the DCPD-type epoxy compound and curing agent may be 10 to 70 wt %, and preferably, 20 to 50 wt % of the total epoxy resin composition, and the content of the inorganic filler may be 30 to 90 wt %, and preferably 50 to 80 wt % of the total epoxy resin composition. When the content of the epoxy compound and the curing agent is included in the range from 10 to 70 wt % of the total epoxy resin composition, a satisfactory adhesive strength may be obtained, and the control of a thickness may be facilitated. Also, when the content of the inorganic filler is 30 to 90 wt %, the high thermal conductive property, low thermal expansion property and high temperature thermal resistance of the epoxy resin composition may be improved. The high thermal conductive property, low thermal expansion property and high temperature thermal resistance may be improved as the content of the inorganic filler is increased. However, the above-described properties are not improved by the volume fraction of the inorganic filler, and are dramatically improved with a specific content of the inorganic filler. On the other hand, when the content of the inorganic filler is more than 90 wt %, viscosity is increased, and thus moldability is degraded.

The DCPD-type epoxy compound included in the epoxy resin composition according to the fourth exemplary embodiment may be, for example, at least one of Formulas 5 to 7. However, the present invention is not limited thereto, and various DCPD-type epoxy compounds, rather than Formulas 5 to 7, may be included.

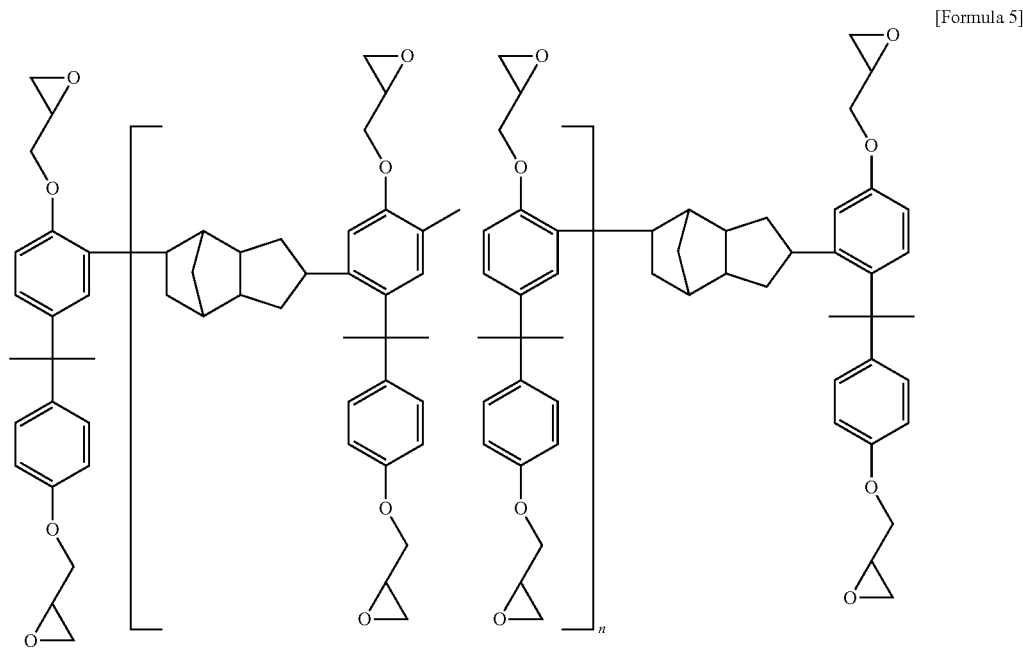

[Formula 5]

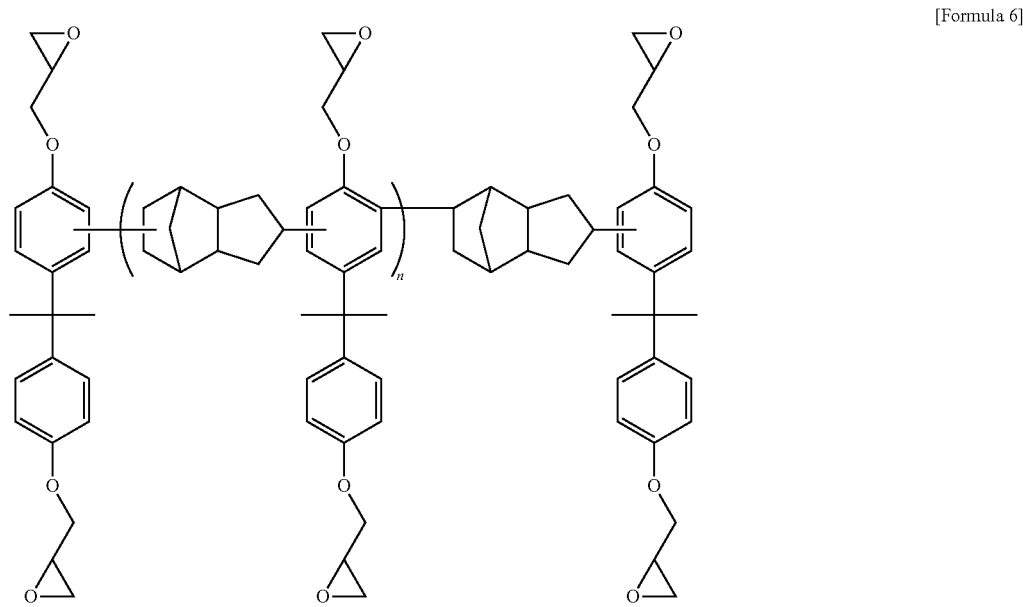

[Formula 6]

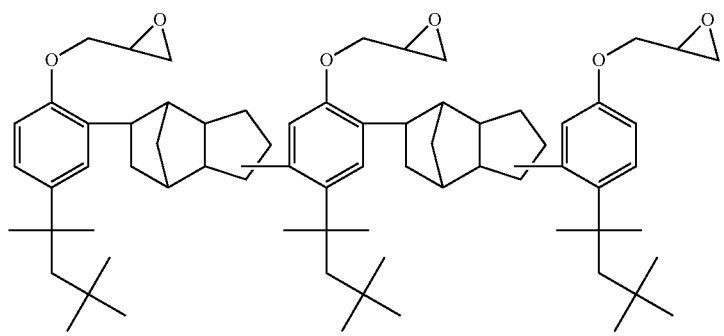

[Formula 7]

In addition, the epoxy resin composition according to the fourth exemplary embodiment may further include at least one of a bisphenol-type epoxy compound, a cyclic epoxy compound, a novolac-type epoxy compound, an aliphatic epoxy compound, and a modified epoxy compound thereof. When the epoxy resin composition according to the fourth exemplary embodiment further includes a bisphenol-type epoxy compound, room temperature stability may be increased.

The curing agent included in the epoxy resin composition according to the fourth exemplary embodiment may include at least one of an amine-based curing agent, a xylol-based curing agent, an acid anhydride-based curing agent, a phenol-based curing agent, a DCPD-based curing agent and a TCPD-based curing agent. For example, the curing agent included in an epoxy resin composition according to an exemplary embodiment of the present invention may be at least one of dicyandiamide of Formula 8, diaminodiphenylsulfone of Formula 9, and 6-H-dibenz[c,e][1,2]oxaphosphorin-6-[2,5-bis(oxiranylmethoxy)phenyl]-6-oxide-aminotriazine novolac (DOPO-ATN) of Formula 10.

of the curing agent with respect to 1 equivalent of the DCPD-type epoxy compound. For example, the content of the curing agent of Formula 8 may be 0.1 to 10 parts by weight, preferably, 1 to 6 parts by weight, and more preferably, 2 to 4 parts by weight with respect to 10 parts by weight of the DCPD-type epoxy compound of Formula 5. When the epoxy compound and the curing agent are included in such a numerical range, a satisfactory adhesive strength may be obtained, and the control of a thickness may be facilitated.

The epoxy resin composition according to the fourth exemplary embodiment may further include a curing accelerator. The curing accelerator may be, for example, an amine-based curing accelerator, an imidazole-based curing accelerator, an urea-based curing accelerator, or an acid-based curing accelerator, and specifically, a tertiary amine such as 1,8-diazabicyclo(5,4,0)undecene-7, triethylenediamine, benzyldimethylamine, triethanolamine, dimethylaminoethanol or tris(dimethylaminomethyl)phenol, or an imidazole such as 2-methylimidazole, 2-phenylimidazole, 2-phenyl-4-methylimidazole or 2-heptadecylimidazole.

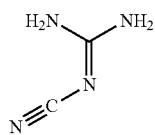

[Formula 8]

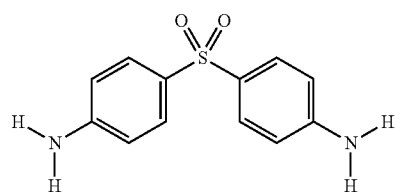

[Formula 9]

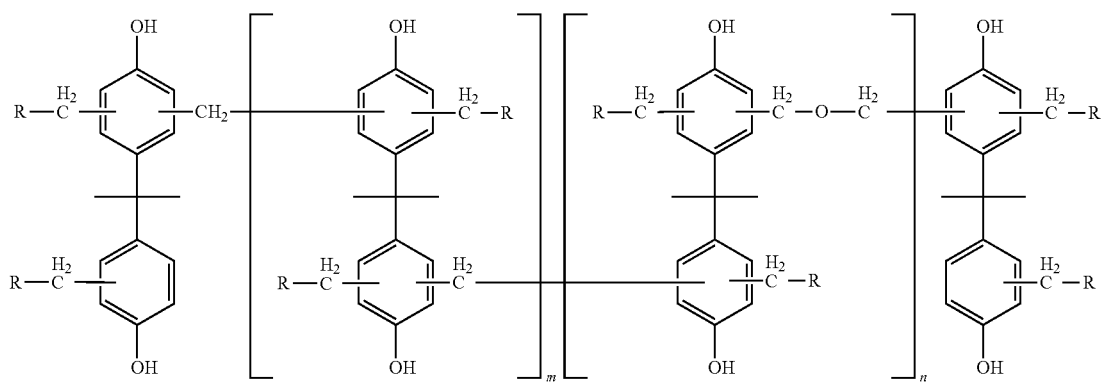

[Formula 10]

The epoxy resin composition according to the fourth exemplary embodiment may include 0.6 to 1.1 equivalents Formula 11 is an example of the imidazole-type curing accelerator.

[Formula 11]

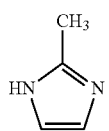

The epoxy resin composition according to the fourth exemplary embodiment includes an inorganic filler including planar boron nitride. The thickness of an insulating layer of a multi-layer printed circuit board according to an exemplary embodiment of the present invention is 30 to 65 µm. Here, D95 of the inorganic filler of the epoxy resin composition included in the insulating layer has to be limited to 90% or less of the thickness of the insulating layer. It is because moldability is degraded and the adhesive performance to the circuit pattern is degraded, when the D95 of the inorganic filler is more than 90% of the thickness of the insulating layer. Meanwhile, as a particle diameter is decreased, the spherical inorganic filler has a larger specific surface area, and a contact area with the epoxy compound is increased. Accordingly, since the epoxy compound has many hydroxyl groups, a dielectric constant is increased. When the epoxy resin composition according to the fourth exemplary embodiment includes the planar boron nitride, a low dielectric constant may be maintained due to a low particle diameter and a small specific surface area. Here, the planar boron nitride may have D50 in a length direction of 8 µm or more, and preferably, 8 to 30 µm. When the D50 of the planar boron nitride in the length direction is within the above-described numerical range, an epoxy resin composition having a low dielectric constant and easily molded may be obtained.

Here, the content of the planar boron nitride may be 10 to 65 wt % of the total epoxy resin composition. When the content of the planar boron nitride is less than 10 wt % of the total epoxy resin composition, the dielectric constant of the epoxy resin composition is increased. Also, when the content of the planar boron nitride is more than 65 wt % of the total epoxy resin composition, a pore is generated, and thus peel strength is decreased.

The epoxy resin composition according to the fourth exemplary embodiment may further include at least one of a ceramic-based inorganic filler including at least one of aluminum oxide, aluminum nitride, spherical boron nitride, silicon nitride, silicon carbide, beryllium oxide and cerium oxide, a carbon-based inorganic filler including at least one of diamond, carbon nanotubes and graphene, and insulated metal particles.

Here, the content of at least one of the ceramic-based inorganic filler and the carbon-based inorganic filler may be 1.53 to 65 parts by weight, preferably, 5 to 50 parts by weight, and more preferably, 10 to 30 parts by weight with respect to 10 parts by weight of the planar boron nitride. When the planar boron nitride and at least one of the ceramic-based inorganic filler and the carbon-based inorganic filler are included within the above-described numerical range, an epoxy resin composition having a high thermal conductivity and a low dielectric constant may be obtained.

According to the fourth exemplary embodiment, the epoxy compound, the curing agent and the inorganic filler may be mixed using a ball mill, impeller mixing, a bead mill, a basket mill, a planetary mill, a dyno mill, or a 3-roll mill. Here, for uniform dispersion, a solvent and a dispersing agent may be added. The solvent may be added to control viscosity, and the viscosity of the solvent may be 1 to 100,000 cps. The solvent may include, for example, at least one of water, methanol, ethanol, isopropanol, butylcarbitol, MEK, toluene, xylene, diethyleneglycol, formamide, α-terpineol, γ-butyrolactone, methyl cellosolve, propylmethyl cellosolve, cyclopentanone, butyl cellosolve (BCE), and dibasic ester (DBE). Also, the dispersing agent may be selected from the group consisting of a non-ionic surfactant, a cationic surfactant, an anionic surfactant, octylalcohol, and acrylic and urethane-based polymers.

The epoxy resin composition according to the fourth exemplary embodiment may further include a silane-based additive to increase binding between particles. The silane-based additive may be, for example, 1-trimethylsilylbutlyne-3-ol, allyltrimethylsilane, trimethylsilyl methanesulfonate, trimethylsilyl trichloroacetate, methyl trimethylsilyl acetate, or trimethylsilyl propionic acid.

The epoxy resin composition according to the fourth exemplary embodiment may further include phosphorus (P) to increase flame retardancy. The content of the phosphorus may be 0.5 to 4 wt % of the epoxy compound, curing agent and curing accelerator.

When the epoxy resin composition according to the fourth exemplary embodiment is applied to the insulating layer of the multi-layer printed circuit board, 15 to 80% of insulating layers of a plurality of insulating layers, for example, an N number of insulating layers may include the epoxy resin composition according to the fourth exemplary embodiment. When the insulating layers including the epoxy resin composition according to the fourth exemplary embodiment are included at less than 15% of the N number of insulating layers, a decrease in surface temperature of the printed circuit board may not be obtained. Also, when the insulating layers including the epoxy resin composition according to the fourth exemplary embodiment are included at more than 80% of the N number of insulating layers, it is difficult to process the printed circuit board.

Here, the present invention will be described in further detail with reference to examples and comparative examples.

Example 4-1

19.3 wt % of the DCPD-type epoxy compound of Formula 5, 5.5 wt % of the dicyandiamide of Formula 8 and 0.2 wt % of the imidazole-based curing accelerator of Formula 11 were dissolved in MEK for 20 minutes, 40 wt % of aluminum oxide and 35 wt % of planar boron nitride (D50 in a length direction: 10 to 20 µm) were added, and the resulting solution was stirred for 2 hours. After the stirring, a copper plate was coated with the resulting solution, and pressurized at 150° C. for 1.5 hours, thereby obtaining an epoxy resin composition of Example 4-1.

Comparative Example 4-1

19.3 wt % of the DCPD-type epoxy compound of Formula 5, 5.5 wt % of the dicyandiamide of Formula 8 and 0.2 wt % of the imidazole-based curing accelerator of Formula 11 were dissolved in MEK for 20 minutes, 75 wt % of aluminum oxide was added, and the resulting solution was stirred for 2 hours. After the stirring, a copper plate was coated with the resulting solution, and pressurized at 150° C. for 1.5 hours, thereby obtaining an epoxy resin composition of Comparative Example 4-1.

Comparative Example 4-2

19.3 wt % of the DCPD-type epoxy compound of Formula 5, 5.5 wt % of the dicyandiamide of Formula 8 and 0.2 wt % of the imidazole-based curing accelerator of Formula 11 were dissolved in MEK for 20 minutes, 70 wt % of aluminum oxide and 5 wt % of planar boron nitride (D50 in a length direction: 10 to 20 μm) were added, and the resulting solution was stirred for 2 hours. After the stirring, a copper plate was coated with the resulting solution, and pressurized at 150° C. for 1.5 hours, thereby obtaining an epoxy resin composition of Comparative Example 4-2.

Comparative Example 4-3

19.3 wt % of the DCPD-type epoxy compound of Formula 5, 5.5 wt % of the dicyandiamide of Formula 8 and 0.2 wt % of the imidazole-based curing accelerator of Formula 11 were dissolved in MEK for 20 minutes, 5 wt % of aluminum oxide and 70 wt % of planar boron nitride (D50 in a length direction: 10 to 20 μm) were added, and the resulting solution was stirred for 2 hours. After the stirring, a copper plate was coated with the resulting solution, and pressurized at 150° C. for 1.5 hours, thereby obtaining an epoxy resin composition of Comparative Example 4-3.

Comparative Example 4-4

19.3 wt % of the novolac-type epoxy compound of Formula 12, 5.5 wt % of the dicyandiamide of Formula 8 and 0.2 wt % of the imidazole-based curing accelerator of Formula 11 were dissolved in MEK for 20 minutes, 40 wt % of aluminum oxide and 35 wt % of planar boron nitride (D50 in a length direction: 10 to 20 μm) were added, and the resulting solution was stirred for 2 hours. After the stirring, a copper plate was coated with the resulting solution, and pressurized at 150° C. for 1.5 hours, thereby obtaining an epoxy resin composition of Comparative Example 4-4.

[Formula 12]

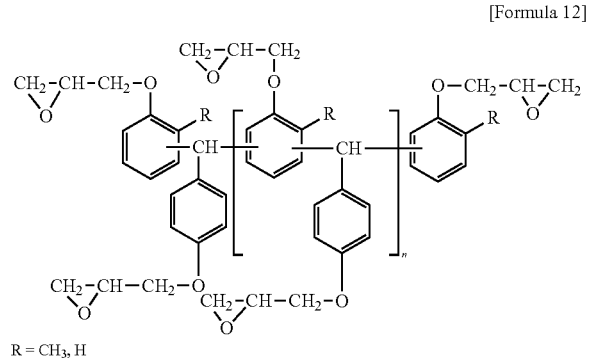

R = CH$_3$, H

Comparative Example 4-5

19.3 wt % of the DCPD-type epoxy compound of Formula 5, 5.5 wt % of the dicyandiamide of Formula 8 and 0.2 wt % of the imidazole-based curing accelerator of Formula 11 were dissolved in MEK for 20 minutes, 40 wt % of aluminum oxide and 35 wt % of planar boron nitride (D50 in a length direction: 5 μm) were added, and the resulting solution was stirred for 2 hours. After the stirring, a copper plate was coated with the resulting solution, and pressurized at 150° C. for 1.5 hours, thereby obtaining an epoxy resin composition of Comparative Example 4-5.

Comparative Example 4-6

19.3 wt % of the DCPD-type epoxy compound of Formula 5, 5.5 wt % of the dicyandiamide of Formula 8 and 0.2 wt % of the imidazole-based curing accelerator of Formula 11 were dissolved in MEK for 20 minutes, 75 wt % of glass fiber was added, and the resulting solution was stirred for 2 hours. After the stirring, a copper plate was coated with the resulting solution, and pressurized at 150° C. for 1.5 hours, thereby obtaining an epoxy resin composition of Comparative Example 4-6.

Experimental Example

After the epoxy resin compositions obtained from Example 4-1 and Comparative Examples 4-1 to 4-6 were cured, thermal conductivity was measured using a thermal conductivity meter according to ASTM E1461, a dielectric constant was measured using IPC-TM-650 2.5.5.9, and peel strength was measured using IPC-TM-650 2.4.8.

Table 10 shows the comparison results of the thermal conductivity, dielectric constant and peel strength between examples and comparative examples.

TABLE 10

| Experiment No. | Thermal conductivity (W/mK) | Dielectric constant (@1 GHz) | Peel strength (Kgf/cm @1 oz) |
|---|---|---|---|
| Example 4-1 | 5.0 | 3.7 | 1.5 |
| Comparative Example 4-1 | 3.5 | 5.5 | 1.5 |
| Comparative Example 4-2 | 3.6 | 5.4 | 1.5 |
| Comparative Example 4-3 | 5.7 | 3.0 | 0.3 |
| Comparative Example 4-4 | 3.9 | 4.4 | 1.5 |
| Comparative Example 4-5 | 4.5 | 4.6 | 1.5 |
| Comparative Example 4-6 | 0.3 | 3.7 | 1.5 |

Referring to Table 10, it can be seen that the epoxy resin composition according to the fourth exemplary embodiment as described in Example 4-1 has a thermal conductivity of 4 w/mK or more, a dielectric constant at 1 GHz of 4 or less, and a peel strength at 1 oz of 1 kgf/cm or more.

On the other hand, it can be seen that Comparative Examples 4-1 and 4-2 in which planar boron nitride is not included or included at less than 10 wt % of the total epoxy resin composition have a dielectric constant higher than 4, and thus are not suitable to be used for an insulating layer. Also, it can be seen that Comparative Example 4-3 in which planar boron nitride is included at more than 65 wt % of the total epoxy resin composition has a peel strength of 1 kgf/cm due to the generation of pores.

Although the inorganic filler including planar boron nitride is included at the same content as in Example 4-1, it can be seen that, in Comparative Example 4-4 using a novolac-type epoxy resin and Comparative Example 4-5 using planar boron nitride having the same composition ratio as in Example 4-1 but D50 in a length direction of less than 8 μm, a dielectric constant is higher than 4. Also, it can be seen that, in Comparative Example 4-6 including glass fiber, a dielectric constant is 4 or less, but thermal conductivity is low.

Hereinafter, the comparison results of heat dissipating performance of printed circuit boards in which some insulating layers include an epoxy resin composition according to an exemplary embodiment of the present invention will be described.

Hereinafter, in Table 11, an epoxy resin composition refers to the epoxy resin composition of Example 4-1, and FR-4 refers to the epoxy resin composition of Comparative Example 4-6.

Thermal stress was applied 10 cycles by floating the printed circuit boards according to the examples and the comparative examples on 288° C. solder for 10 seconds per each cycle. Here, the cycles at which the circuit pattern layer and the insulating layer are separated from each other, or a pore starts swelling were recorded.

An elevated temperature is the result obtained by attaching a ceramic-based heat source on which a thermocouple is fixed to the printed circuit boards of the examples and the comparative examples and measuring a temperature of the heat source at room temperature (25° C.). The same output (voltage×ampere) was applied to the printed circuit boards of the examples and comparative examples, followed by measuring a temperature. The result obtained by subtracting the temperature measured at room temperature from the temperature measured after the application of the output was determined as an elevated temperature.

Table 11 shows the comparison results of heat dissipating performance between ten-layer printed circuit boards.

As shown in Table 11, it can be seen that all of the ten-layer printed circuit boards of Examples 4-2 to 4-3 and Comparative Examples 4-7 to 4-8 can resist 10 cycles of thermal stress. However, compared to Comparative Example 4-8 in which all of the insulating layers include FR-4 (elevated temperature: 70.1° C.), Examples 4-2 to 4-3 in which all or some of the insulating layers include an epoxy resin composition and Comparative Example 4-7 have a low elevated temperature. Accordingly, it can be seen that the printed circuit boards of Examples 4-2 to 4-3 and Comparative Example 4-7 have a greater heat dissipating performance than Comparative Example 4-8. However, in the printed circuit board of Comparative Example 4-7 in which more than 80% of the insulating layers include the epoxy resin composition of the present invention, an elevated temperature is low, but a defect rate in processing, which is caused by vias, is increased.

Alternatively, the epoxy resin composition included in an insulating layer of a printed circuit board according to an exemplary embodiment of the present invention may be an epoxy resin composition according to a fifth exemplary embodiment.

TABLE 11

| Cross-sectional structure | Example 4-2 Type | Thickness [mm] | Example 4-3 Type | Thickness [mm] | Comparative Example 4-7 Type | Thickness [mm] | Comparative Example 4-8 Type | Thickness [mm] |
|---|---|---|---|---|---|---|---|---|
| Circuit pattern layer (1210-10) | Cu | 0.025 | Cu | 0.025 | Cu | 0.025 | Cu | 0.025 |
| Insulating layer (1220-9) | Epoxy resin composition | 0.060 | Epoxy resin composition | 0.060 | Epoxy resin composition | 0.060 | FR-4 | 0.060 |
| Circuit pattern layer (1210-9) | Cu | 0.020 | Cu | 0.020 | Cu | 0.020 | Cu | 0.020 |
| Insulating layer (1220-8) | FR-4 | 0.060 | Epoxy resin composition | 0.060 | Epoxy resin composition | 0.060 | FR-4 | 0.060 |
| Circuit pattern layer (1210-8) | Cu | 0.020 | Cu | 0.020 | Cu | 0.020 | Cu | 0.020 |
| Insulating layer (1220-7) | FR-4 | 0.060 | FR-4 | 0.060 | Epoxy resin composition | 0.060 | FR-4 | 0.060 |
| Circuit pattern layer (1210-7) | Cu | 0.020 | Cu | 0.020 | Cu | 0.020 | Cu | 0.020 |
| Insulating layer (1220-6) | FR-4 | 0.060 | FR-4 | 0.060 | Epoxy resin composition | 0.060 | FR-4 | 0.060 |
| Circuit pattern layer (1210-6) | Cu | 0.020 | Cu | 0.020 | Cu | 0.020 | Cu | 0.020 |
| Insulating layer (1220-5) | FR-4 | 0.060 | FR-4 | 0.060 | FR-4 | 0.060 | FR-4 | 0.060 |
| Circuit pattern layer (1210-5) | Cu | 0.020 | Cu | 0.020 | Cu | 0.020 | Cu | 0.020 |
| Insulating layer (1220-4) | FR-4 | 0.060 | FR-4 | 0.060 | Epoxy resin composition | 0.060 | FR-4 | 0.060 |
| Circuit pattern layer (1210-4) | Cu | 0.020 | Cu | 0.020 | Cu | 0.020 | Cu | 0.020 |
| Insulating layer (1220-3) | FR-4 | 0.060 | FR-4 | 0.060 | Epoxy resin composition | 0.060 | FR-4 | 0.060 |
| Circuit pattern layer (1210-3) | Cu | 0.020 | Cu | 0.020 | Cu | 0.020 | Cu | 0.020 |
| Insulating layer (1220-2) | FR-4 | 0.060 | Epoxy resin composition | 0.060 | Epoxy resin composition | 0.060 | FR-4 | 0.060 |
| Circuit pattern layer (1210-2) | Cu | 0.020 | Cu | 0.020 | Cu | 0.020 | Cu | 0.020 |
| Insulating layer (1220-1) | Epoxy resin composition | 0.060 | Epoxy resin composition | 0.060 | Epoxy resin composition | 0.060 | FR-4 | 0.060 |
| Circuit pattern layer (1210-1) | Cu | 0.025 | Cu | 0.025 | Cu | 0.025 | Cu | 0.025 |
| Thermal stress | 10 cycles | | 10 cycles | | 10 cycles | | 10 cycles | |
| Elevated temperature (° C.) | 65.6 | | 62.9 | | 56.7 | | 70.1 | |

The epoxy resin composition according to the fifth exemplary embodiment includes an epoxy compound, a curing agent, and an inorganic filler including a hollow filler and boron nitride.

Here, the content of the epoxy compound and the curing agent may be 10 to 70 wt %, and preferably, 20 to 50 wt % of the total epoxy resin composition, and the content of the inorganic filler may be 30 to 90 wt %, and preferably, 50 to 80 wt % of the total epoxy resin composition. When the content of the epoxy compound and the curing agent is 10 to 70 wt % of the total epoxy resin composition, a satisfactory adhesive strength is achieved, and the control of a thickness may be facilitated. In addition, when the content of the inorganic filler is 30 to 90 wt %, the high thermal conductive property, low thermal expansion property and high temperature thermal resistance of the epoxy resin composition may be improved. As the content of the inorganic filler is higher, the high thermal conductive property, low thermal expansion property and high temperature thermal resistance are improved. However, the improvement is achieved by the volume fraction of the inorganic filler, and dramatically achieved with a specific content thereof. On the other hand, when the content of the inorganic filler is more than 90 wt %, viscosity is increased, and thus moldability is degraded.

The epoxy compound included in the epoxy resin composition according to the fifth exemplary embodiment may include at least one of a DCPD-type epoxy compound and a novolac-type epoxy compound.

The DCPD-type epoxy compound may include, for example, the compound of Formula 13. The present invention is not limited thereto, and rather than the compound of Formula 13, various DCPD-type epoxy compounds may be included.

The novolac-type epoxy compound may include, for example, the compound of Formula 14. The present invention is not limited thereto, and rather than the compound of Formula 14, various novolac-type epoxy compounds may be included.

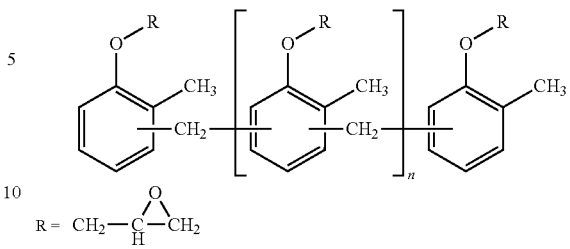

[Formula 14]

Also, the epoxy resin composition according to the fifth exemplary embodiment may further include an amorphous epoxy compound. The content of the amorphous epoxy compound may be 1 to 40 parts by weight with respect to 10 parts by weight of the DCPD-type epoxy compound or novolac-type epoxy compound. When the amorphous epoxy compound is included at the above-described ratio, room temperature stability may be increased.

An example of the amorphous epoxy compound is shown in Formula 15. Formula 15 represents a bisphenol A-type epoxy compound.

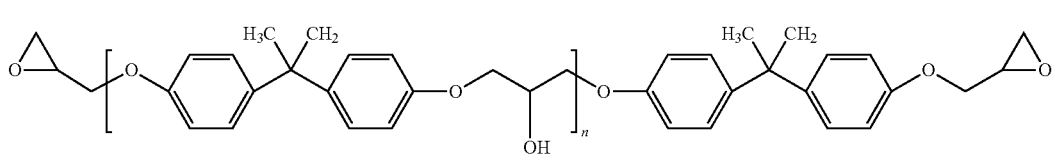

[Formula 15]

The curing agent included in the epoxy resin composition according to the fifth exemplary embodiment may include at least one of an amine-based curing agent, a xylol-based curing agent, an acid anhydride-based curing agent, a phenol-based curing agent, a DCPD-based curing agent, and a TCPD-based curing agent. For example, the curing agent included in the epoxy resin composition according to the fifth exemplary embodiment may be at least one of dicyandiamide of Formula 8, diaminodiphenylsulfone of Formula 9, and DOPO-ATN of Formula 10.

The epoxy resin composition according to the fifth exemplary embodiment may include 0.6 to 1.1 equivalents of the curing agent with respect to 1 equivalent of the epoxy compound. For example, with respect to 10 parts by weight of the DCPD-type epoxy compound of Formula 13, the content of the curing agent of Formula 8 may be 0.1 to 10 parts by weight, preferably, 1 to 6 parts by weight, and more preferably, 2 to 4 parts by weight. When the epoxy compound and the curing agent are included within the above-described numerical range, a satisfactory adhesive strength is achieved, and the control of a thickness may be facilitated.

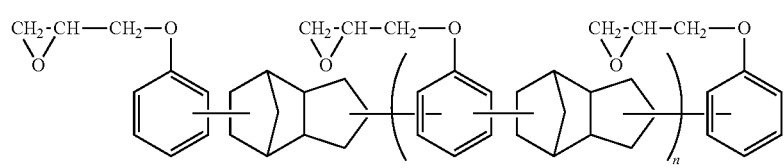

[Formula 13]

The epoxy resin composition according to the fifth exemplary embodiment may further include a curing accelerator.

Figure 14:
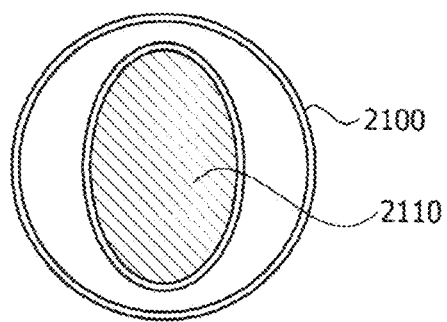
FIG. 14 is an example of the cross-section of a hollow glass bubble.

The epoxy resin composition according to the fifth exemplary embodiment includes an inorganic filler including a hollow filler and boron nitride. Here, the hollow filler may have a hollow glass bubble (HGB). The cross-section of the HGB is shown in FIG. 14. Referring to FIG. 14, the HGB 2100 has an air gap 2110 in the middle, and has a density of approximately 0.6 g/cc, a hardness of approximately 200 MPa, and a diameter of 10 to 30 µm, wherein an air volume of the air gap is 70 to 90 vol % of the HGB. When the HGB is included as the inorganic filler as described above, the dielectric constant of the epoxy resin composition may be reduced. Particularly, when the diameter and the air volume of the HGB are within such a numerical range, a high thermal conductivity and a low dielectric constant may be maintained.

Here, 0.1 to 100 parts by weight of the boron nitride may be included with respect to 10 parts by weight of the hollow filler. When the hollow filler and the boron nitride are included within such a numerical range, an epoxy resin composition having a high thermal conductivity and a low dielectric constant may be obtained.

Figure 15:
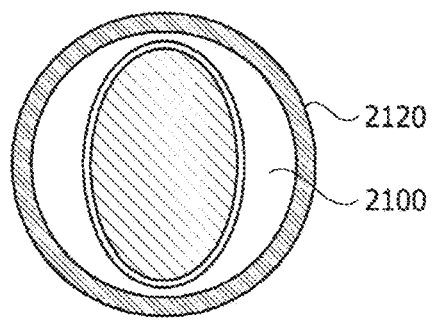
FIG. 15 shows the cross-section of a hollow glass bubble coated with aluminum oxide.

Also, the surface of the HGB may be coated with aluminum oxide. FIG. 15 is the cross-section of the HGB coated with aluminum oxide (Al-HGB). Referring to FIG. 15, the HGB 2100 is coated to be 5 to 20 µm thick with the aluminum oxide 2120. When the aluminum oxide is applied at a thickness of 5 to 20 µm, the thermal conductive performance of the HGB may be increased.

In addition, according to the fifth exemplary embodiment, the inorganic filler may further include aluminum oxide. Here, with respect to 10 parts by weight of the HGB, the content of the boron nitride may be 1 to 20 parts by weight, and the content of the aluminum oxide may be 1 to 35 parts by weight. The HGB, boron nitride and aluminum oxide are included within such numerical ranges, an epoxy resin composition having a high thermal conductivity and a low dielectric constant may be obtained.

In addition, the epoxy resin composition according to the fifth exemplary embodiment may further include at least one of a ceramic-based inorganic filler including at least one of aluminum nitride, silicon nitride, silicon carbide, beryllium oxide and cerium oxide, a carbon-based inorganic filler including at least one of diamond, carbon nanotubes and graphene, and insulation metal particles.

Hereinafter, the present invention will be described in further detail with reference to examples and comparative examples.

Example 5-1

19.3 wt % of the DCPD-type epoxy compound of Formula 13, 5.5 wt % of the dicyandiamide of Formula 8 and 0.2 wt % of the imidazole-based curing accelerator of Formula 11 were dissolved in MEK for 30 minutes, 20 wt % of HGB and 55 wt % of boron nitride were added, and the resulting solution was stirred for 2 hours. After the stirring, a copper plate was coated to a thickness of 60 urn with the solution, cured at 120° C. for 1.5 hours, and pressurized at 40 kgf/cm² at 180° C. for 1.5 hours, thereby obtaining an epoxy resin composition of Example 5-1.

Example 5-2

19.3 wt % of the DCPD-type epoxy compound of Formula 13, 5.5 wt % of the dicyandiamide of Formula 8 and 0.2 wt % of the imidazole-based curing accelerator of Formula 11 were dissolved in MEK for 30 minutes, 20 wt % of Al-HGB and 55 wt % of boron nitride were added, and the resulting solution was stirred for 2 hours. After the stirring, a copper plate was coated to a thickness of 60 µm with the solution, cured at 120° C. for 1.5 hours, and pressurized at 40 kgf/cm² at 180° C. for 1.5 hours, thereby obtaining an epoxy resin composition of Example 5-2.

Example 5-3

19.3 wt % of the DCPD-type epoxy compound of Formula 13, 5.5 wt % of the dicyandiamide of Formula 8 and 0.2 wt % of the imidazole-based curing accelerator of Formula 11 were dissolved in MEK for 30 minutes, 20 wt % of Al-HGB, 40 wt % of boron nitride and 15 wt % of aluminum oxide were added, and the resulting solution was stirred for 2 hours. After the stirring, a copper plate was coated to a thickness of 60 µm with the solution, cured at 120° C. for 1.5 hours, and pressurized at 40 kgf/cm² at 180° C. for 1.5 hours, thereby obtaining an epoxy resin composition of Example 5-3.

Example 5-4

19.3 wt % of the DCPD-type epoxy compound of Formula 13, 5.5 wt % of the dicyandiamide of Formula 8 and 0.2 wt % of the imidazole-based curing accelerator of Formula 11 were dissolved in MEK for 30 minutes, 15 wt % of Al-HGB, 25 wt % of boron nitride and 35 wt % of aluminum oxide were added, and the resulting solution was stirred for 2 hours. After the stirring, a copper plate was coated to a thickness of 60 µm with the solution, cured at 120° C. for 1.5 hours, and pressurized at 40 kgf/cm² at 180° C. for 1.5 hours, thereby obtaining an epoxy resin composition of Example 5-4.

Example 5-5

19.3 wt % of the DCPD-type epoxy compound of Formula 13, 5.5 wt % of the dicyandiamide of Formula 8 and 0.2 wt % of the imidazole-based curing accelerator of Formula 11 were dissolved in MEK for 30 minutes, 20 wt % of Al-HGB, 25 wt % of boron nitride and 30 wt % of aluminum oxide were added, and the resulting solution was stirred for 2 hours. After the stirring, a copper plate was coated to a thickness of 60 µm with the solution, cured at 120° C. for 1.5 hours, and pressurized at 40 kgf/cm² at 180° C. for 1.5 hours, thereby obtaining an epoxy resin composition of Example 5-5.

Comparative Example 5-1

19.3 wt % of the DCPD-type epoxy compound of Formula 13, 5.5 wt % of the dicyandiamide of Formula 8 and 0.2 wt % of the imidazole-based curing accelerator of Formula 11 were dissolved in MEK for 30 minutes, 75 wt % of HGB was added, and the resulting solution was stirred for 2 hours. After the stirring, a copper plate was coated to a thickness of 60 µm with the solution, cured at 120° C. for 1.5 hours, and pressurized at 40 kgf/cm² at 180° C. for 1.5 hours, thereby obtaining an epoxy resin composition of Comparative Example 5-1.

Comparative Example 5-2

19.3 wt % of the DCPD-type epoxy compound of Formula 13, 5.5 wt % of the dicyandiamide of Formula 8 and 0.2 wt % of the imidazole-based curing accelerator of Formula 11 were dissolved in MEK for 30 minutes, 75 wt % of boron nitride was added, and the resulting solution was stirred for 2 hours. After the stirring, a copper plate was coated to a thickness of 60 μm with the solution, cured at 120° C. for 1.5 hours, and pressurized at 40 kgf/cm² at 180° C. for 1.5 hours, thereby obtaining an epoxy resin composition of Comparative Example 5-2.

Comparative Example 5-3

19.3 wt % of the DCPD-type epoxy compound of Formula 13, 5.5 wt % of the dicyandiamide of Formula 8 and 0.2 wt % of the imidazole-based curing accelerator of Formula 11 were dissolved in MEK for 30 minutes, 20 wt % of HGB and 55 wt % of aluminum oxide were added, and the resulting solution was stirred for 2 hours. After the stirring, a copper plate was coated to a thickness of 60 un with the solution, cured at 120° C. for 1.5 hours, and pressurized at 40 kgf/cm² at 180° C. for 1.5 hours, thereby obtaining an epoxy resin composition of Comparative Example 5-3.

Comparative Example 5-4

19.3 wt % of the DCPD-type epoxy compound of Formula 13, 5.5 wt % of the dicyandiamide of Formula 8 and 0.2 wt % of the imidazole-based curing accelerator of Formula 11 were dissolved in MEK for 30 minutes, 75 wt % of Al-HGB was added, and the resulting solution was stirred for 2 hours. After the stirring, a copper plate was coated to a thickness of 60 μm with the solution, cured at 120° C. for 1.5 hours, and pressurized at 40 kgf/cm² at 180° C. for 1.5 hours, thereby obtaining an epoxy resin composition of Comparative Example 5-4.

Comparative Example 5-5

19.3 wt % of the DCPD-type epoxy compound of Formula 13, 5.5 wt % of the dicyandiamide of Formula 8 and 0.2 wt % of the imidazole-based curing accelerator of Formula 11 were dissolved in MEK for 30 minutes, 20 wt % of Al-HGB and 55 wt % of aluminum oxide were added, and the resulting solution was stirred for 2 hours. After the stirring, a copper plate was coated to a thickness of 60 μm with the solution, cured at 120° C. for 1.5 hours, and pressurized at 40 kgf/cm² at 180° C. for 1.5 hours, thereby obtaining an epoxy resin composition of Comparative Example 5-5.

Comparative Example 5-6

19.3 wt % of the DCPD-type epoxy compound of Formula 13, 5.5 wt % of the dicyandiamide of Formula 8 and 0.2 wt % of the imidazole-based curing accelerator of Formula 11 were dissolved in MEK for 30 minutes, 15 wt % of HGB, 25 wt % of boron nitride and 35 wt % of aluminum oxide were added, and the resulting solution was stirred for 2 hours. After the stirring, a copper plate was coated to a thickness of 60 μm with the solution, cured at 120° C. for 1.5 hours, and pressurized at 40 kgf/cm² at 180° C. for 1.5 hours, thereby obtaining an epoxy resin composition of Comparative Example 5-6.

Comparative Example 5-7

19.3 wt % of the DCPD-type epoxy compound of Formula 13, 5.5 wt % of the dicyandiamide of Formula 8 and 0.2 wt % of the imidazole-based curing accelerator of Formula 11 were dissolved in MEK for 30 minutes, 20 wt % of HGB, 25 wt % of boron nitride and 30 wt % of aluminum oxide were added, and the resulting solution was stirred for 2 hours. After the stirring, a copper plate was coated to a thickness of 60 μm with the solution, cured at 120° C. for 1.5 hours, and pressurized at 40 kgf/cm² at 180° C. for 1.5 hours, thereby obtaining an epoxy resin composition of Comparative Example 5-7.

Comparative Example 5-8

19.3 wt % of the DCPD-type epoxy compound of Formula 13, 5.5 wt % of the dicyandiamide of Formula 8 and 0.2 wt % of the imidazole-based curing accelerator of Formula 11 were dissolved in MEK for 30 minutes, 10 wt % of Al-HGB, 25 wt % of boron nitride and 40 wt % of aluminum oxide were added, and the resulting solution was stirred for 2 hours. After the stirring, a copper plate was coated to a thickness of 60 μm with the solution, cured at 120° C. for 1.5 hours, and pressurized at 40 kgf/cm² at 180° C. for 1.5 hours, thereby obtaining an epoxy resin composition of Comparative Example 5-8.

Experimental Example

After the epoxy resin compositions obtained from Examples 5-1 to 5-5 and Comparative Examples 5-1 to 5-8 were cured, thermal conductivity was measured using a thermal conductivity meter according to ASTM E1461, and a dielectric constant was measured using IPC-TM-650 2.5.5.9.

The HGBs obtained from Examples 5-1 to 5-5 and Comparative Examples 5-1 to 5-8 have a diameter of 10 to 30 μm and an air volume of 70 to 90 vol %, and the thickness of the aluminum oxide with which Al-HGB is coated is 5 to 20 μm.

Table 12 shows the comparison results of a thermal conductivity and a dielectric constant between the examples and the comparative examples.

TABLE 12

| Experiment No. | Thermal conductivity (w/mK) | Dielectric constant (@1 GHz) |
|---|---|---|
| Example 5-1 | 2.68 | 3.78 |
| Example 5-2 | 3.21 | 3.84 |
| Example 5-3 | 3.51 | 3.90 |
| Example 5-4 | 3.81 | 3.88 |
| Example 5-5 | 3.4 | 3.79 |
| Comparative Example 5-1 | 0.71 | 3.10 |
| Comparative Example 5-2 | 3.67 | 4.23 |
| Comparative Example 5-3 | 1.51 | 3.94 |
| Comparative Example 5-4 | 1.84 | 3.29 |
| Comparative Example 5-5 | 1.78 | 4.04 |
| Comparative Example 5-6 | 2.59 | 3.83 |
| Comparative Example 5-7 | 2.18 | 3.71 |
| Comparative Example 5-8 | 4.01 | 4.02 |

Referring to Table 12, it can be seen that Example 5-1 including the hollow filler (diameter: 10 to 30 μm, air volume: 70 to 90 vol %) and the boron nitride has a thermal conductivity of 2.6 w/mK or more and a dielectric constant (@1 GHz) of 4 or less, and the thermal conductivity which is higher than in Comparative Example 5-1 including the hollow filler and Comparative Example 5-3 including the hollow filler and the aluminum oxide, and the dielectric constant is lower than in Comparative Example 5-2 including the boron nitride.

In addition, it can be seen that Example 5-2 including the aluminum oxide-coated hollow filler (diameter: 10 to 30 µm, air volume: 70 to 90 vol %, coated with aluminum oxide to 5 to 20 µm thick) and the boron nitride has a higher thermal conductivity than Example 5-1 including the uncoated hollow filler (diameter: 10 to 30 µm, air volume: 70 to 90 vol %) and the boron nitride, Comparative Example 5-4 including only the aluminum oxide-coated hollow filler and Comparative Example 5-5 including only the aluminum oxide-coated hollow filler and the aluminum oxide.

Also, it can be seen that Examples 5-3 to 5-5 further including aluminum oxide as well as the aluminum oxide-coated hollow filler as the inorganic filler and the boron nitride have a higher thermal conductivity than Example 5-1 or 5-2. Particularly, it can be seen that Examples 5-4 to 5-5 have a higher thermal conductivity than Comparative Examples 5-6 to 5-7 including the uncoated hollow filler, the boron nitride and the aluminum oxide.

However, although further including the aluminum oxide as well as the aluminum oxide-coated hollow filler as the inorganic filler and the boron nitride, since Comparative Example 5-8 exceeds the numerical range in which 1 to 20 parts by weight of boron nitride and 1 to 35 parts by weight of aluminum oxide are included with respect to 10 parts by weight of the hollow filler, a dielectric constant is 4 or more, and thus it is noted that Comparative Example 5-8 is not suitable to be used for an insulating layer.

Accordingly, as the epoxy resin composition according to the fifth exemplary embodiment is cured and used for an insulating layer, a printed circuit board having a thermal conductivity of 2.6 w/mK or more, and a dielectric constant at 1 GHz of 4 or less.

According to an exemplary embodiment of the present invention, an inorganic filler included in an epoxy resin composition applied to a printed circuit board or a light emitting element module can be obtained. Accordingly, the epoxy resin composition having a satisfactory dispersibility, an excellent electrical insulation, a high peel strength and a high thermal conductivity can be obtained.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. An inorganic filler comprising:
    a boron nitride; and
    a polycyclic aromatic hydrocarbon having a functional group formed on a surface of the boron nitride,
    wherein the polycyclic aromatic hydrocarbon includes at least one selected from the group consisting of naphthalene, anthracene and pyrene,
    wherein the functional group is selected from the group consisting of —OH, —COOH, —HSO$_3$, —NH$_2$CO, Cl, Br, F, C$_1$ to C$_3$ alkyls, C$_2$ to C$_3$ alkenes, and C$_2$ to C$_3$ alkynes,
    wherein the boron nitride includes hexagonal boron nitride formed in a hexagonal lattice by alternately arranging nitrogen atoms and boron atoms,
    wherein the boron nitride is stacked in layers,
    wherein each layer includes a plurality of hexagonal boron nitride arranged on a plane, and
    wherein the polycyclic aromatic hydrocarbon having the functional group is bonded between the plurality of layers.

2. The inorganic filler of claim 1, wherein the inorganic filler includes the boron nitride at 85 to 99 vol % and the polycyclic aromatic hydrocarbon at 1 to 15 vol %.

3. The inorganic filler of claim 2, wherein the inorganic filler includes the boron nitride at 88 to 97 vol % and the polycyclic aromatic hydrocarbon at 3 to 12 vol %.

4. The inorganic filler of claim 1, wherein the polycyclic aromatic hydrocarbon having a functional group is bonded to at least one of the uppermost layer and the lowermost layer of the plurality of layers.

5. The inorganic filler of claim 1, wherein the polycyclic aromatic hydrocarbon includes at least one selected from the group consisting of anthracene and pyrene.

6. The inorganic filler of claim 1, wherein the functional group is selected from the group consisting of —COOH, —HSO$_3$, —NH$_2$CO, Cl, Br, F, C$_1$ to C$_3$ alkyls, C$_2$ to C$_3$ alkenes, and C$_2$ to C$_3$ alkynes.

7. An epoxy resin composition comprising:
    an epoxy compound; and
    an inorganic filler including a boron nitride having a surface on which a polycyclic aromatic hydrocarbon having a functional group is provided,
    wherein the polycyclic aromatic hydrocarbon includes at least one selected from the group consisting of naphthalene, anthracene and pyrene,
    wherein the functional group is selected from the group consisting of —OH, —COOH, —HSO$_3$, —NH$_2$CO, Cl, Br, F, C$_1$ to C$_3$ alkyls, C$_2$ to C$_3$ alkenes, and C$_2$ to C$_3$ alkynes,
    wherein the boron nitride includes hexagonal boron nitride formed in a hexagonal lattice by alternately arranging nitrogen atoms and boron atoms,
    wherein the boron nitride is stacked in layers,
    wherein each layer includes a plurality of hexagonal boron nitride arranged on a plane, and
    wherein the polycyclic aromatic hydrocarbon having the functional group is bonded between the plurality of layers.

8. The epoxy resin composition of claim 7, wherein the boron nitride is included at 85 to 99 vol % and the polycyclic aromatic hydrocarbon is included at 1 to 15 vol % with respect to 100 vol % of the inorganic filler.

9. The epoxy resin composition of claim 7, wherein the volumetric ratio of the epoxy compound to the inorganic filler is 10:30 to 120.

10. The epoxy resin composition of claim 9, wherein the volumetric ratio of the epoxy compound to the inorganic filler is 10:36 to 90.

11. The epoxy resin composition of claim 10, wherein the volumetric ratio of the epoxy compound to the inorganic filler is 10:44 to 60.

12. The epoxy resin composition of claim 7, wherein the polycyclic aromatic hydrocarbon includes at least one selected from the group consisting of anthracene and pyrene.

13. The epoxy resin composition of claim 7, wherein the functional group is selected from the group consisting of —COOH, —HSO$_3$, —NH$_2$CO, Cl, Br, F, C$_1$ to C$_3$ alkyls, C$_2$ to C$_3$ alkenes, and C$_2$ to C$_3$ alkynes.

14. A printed circuit board comprising:
    a substrate;
    an insulating layer formed on the substrate; and
    a circuit pattern formed on the insulating layer,
    wherein the insulating layer includes an epoxy resin composition, which includes an epoxy compound; and
    an inorganic filler including a boron nitride having a surface on which a polycyclic aromatic hydrocarbon having a functional group is provided, wherein the polycyclic aromatic hydrocarbon includes at least one selected from the group consisting of naphthalene, anthracene, and pyrene,
wherein the functional group is selected from the group consisting of —OH, —COOH, —HSO$_3$, —NH$_2$CO, Cl, Br, F, C$_1$ to C$_3$ alkyls, C$_2$ to C$_3$ alkenes, and C$_2$ and C$_3$ alkynes,
wherein the boron nitride includes hexagonal boron nitride formed in a hexagonal lattice by alternately arranging nitrogen atoms and boron atoms,
wherein the boron nitride is stacked in layers,
wherein each layer includes a plurality of hexagonal boron nitride arranged on a plane, and
wherein the polycyclic aromatic hydrocarbon having the functional group is bonded between the plurality of layers provided.

* * * * *